(12) United States Patent
Turner et al.

(10) Patent No.: US 10,314,588 B2
(45) Date of Patent: Jun. 11, 2019

(54) FLUID PENETRABLE BUTTRESS ASSEMBLY FOR A SURGICAL STAPLER

(71) Applicant: Ethicon Endo-Surgery, LLC, Guaynabo, PR (US)

(72) Inventors: Prudence A. Turner, Independence, KY (US); Emily A. Schellin, Cincinnati, OH (US); Michael J. Vendely, Lebanon, OH (US); Trevor J. Barton, Cincinnati, OH (US); Jason L. Harris, Lebanon, OH (US); Charles J. Scheib, Loveland, OH (US); Frederick E. Shelton, IV, Hillsboro, OH (US)

(73) Assignee: Ethicon LLC, Guaynabo, PR (US)

( * ) Notice: Subject to any disclaimer, the term of this patent is extended or adjusted under 35 U.S.C. 154(b) by 468 days.

(21) Appl. No.: 14/926,029

(22) Filed: Oct. 29, 2015

(65) Prior Publication Data

US 2017/0119389 A1    May 4, 2017

(51) Int. Cl.
*A61B 17/10*  (2006.01)
*A61B 17/068* (2006.01)
(Continued)

(52) U.S. Cl.
CPC .......... *A61B 17/105* (2013.01); *A61B 17/068* (2013.01); *A61B 17/07292* (2013.01);
(Continued)

(58) Field of Classification Search
CPC ................. A61B 17/105; A61B 17/068; A61B 17/07292
(Continued)

(56) References Cited

U.S. PATENT DOCUMENTS

| 4,805,823 A | 2/1989 | Rothfuss |
| 5,263,629 A * | 11/1993 | Trumbull ......... A61B 17/07207 |
| | | 128/898 |

(Continued)

FOREIGN PATENT DOCUMENTS

| CA | 2834503 A1 | 11/2012 |
| EP | 1 064 883 A1 | 1/2001 |
| EP | 2 008 595 A2 | 12/2008 |

OTHER PUBLICATIONS

U.S. Appl. No. 62/209,041, filed Aug. 24, 2015.
(Continued)

*Primary Examiner* — Nathaniel Chukwurah
(74) *Attorney, Agent, or Firm* — Frost Brown Todd LLC

(57) ABSTRACT

An apparatus includes an end effector, a cartridge, and a buttress assembly. The end effector includes an anvil and a lower jaw. The anvil is configured to move toward and away from the lower jaw. The lower jaw is configured to receive the cartridge. The cartridge includes a housing, staples disposed in the housing, and a deck disposed over the staples. The buttress assembly is configured to be attached to either the anvil or the cartridge. The buttress assembly includes an adhesive layer, a film layer, and a buttress body. The adhesive layer is configured to adhere to either the anvil or the deck of the cartridge. The adhesive layer is attached to a first side of the film layer. The buttress body is attached to a second side of the film layer such that the film layer is interposed between the adhesive layer and the buttress body.

18 Claims, 13 Drawing Sheets

(51) Int. Cl.
*A61B 17/072* (2006.01)
*A61B 17/00* (2006.01)

(52) U.S. Cl.
CPC ............ *A61B 17/07207* (2013.01); *A61B 2017/00004* (2013.01); *A61B 2017/00398* (2013.01); *A61B 2017/00526* (2013.01); *A61B 2017/00951* (2013.01); *A61B 2017/00964* (2013.01)

(58) Field of Classification Search
USPC .......... 227/176.1, 175.1, 19, 180.1; 606/151, 606/153, 219
See application file for complete search history.

(56) References Cited

U.S. PATENT DOCUMENTS

| | | | |
|---|---|---|---|
| 5,415,334 A | | 5/1995 | Williamson et al. |
| 5,465,895 A | | 11/1995 | Knodel et al. |
| 5,466,231 A | * | 11/1995 | Cercone ............ A61F 13/36 |
| | | | 602/41 |
| 5,597,107 A | | 1/1997 | Knodel et al. |
| 5,632,432 A | | 5/1997 | Schulze et al. |
| 5,673,840 A | | 10/1997 | Schulze et al. |
| 5,704,534 A | | 1/1998 | Huitema et al. |
| 5,792,135 A | | 8/1998 | Madhani et al. |
| 5,814,055 A | | 9/1998 | Knodel et al. |
| 5,817,084 A | | 10/1998 | Jensen |
| 5,878,193 A | | 3/1999 | Wang et al. |
| 6,231,565 B1 | | 5/2001 | Tovey et al. |
| 6,325,810 B1 | * | 12/2001 | Hamilton ......... A61B 17/07207 |
| | | | 227/175.1 |
| 6,364,888 B1 | | 4/2002 | Niemeyer et al. |
| 6,783,524 B2 | | 8/2004 | Anderson et al. |
| 6,978,921 B2 | | 12/2005 | Shelton, IV et al. |
| 7,000,818 B2 | | 2/2006 | Shelton, IV et al. |
| 7,143,923 B2 | | 12/2006 | Shelton, IV et al. |
| 7,303,108 B2 | | 12/2007 | Shelton, IV |
| 7,367,485 B2 | | 5/2008 | Shelton, IV et al. |
| 7,380,695 B2 | | 6/2008 | Doll et al. |
| 7,380,696 B2 | | 6/2008 | Shelton, IV et al. |
| 7,404,508 B2 | | 7/2008 | Smith et al. |
| 7,434,715 B2 | | 10/2008 | Shelton, IV et al. |
| 7,524,320 B2 | | 4/2009 | Tierney |
| 7,691,098 B2 | | 4/2010 | Wallace |
| 7,721,930 B2 | | 5/2010 | McKenna et al. |
| 7,806,891 B2 | | 10/2010 | Nowlin et al. |
| 8,141,762 B2 | | 3/2012 | Bedi et al. |
| 8,210,411 B2 | | 7/2012 | Yates et al. |
| 8,371,491 B2 | | 2/2013 | Huitema et al. |
| 8,408,439 B2 | | 4/2013 | Huang et al. |
| 8,453,914 B2 | | 6/2013 | Laurent et al. |
| 8,479,969 B2 | | 7/2013 | Shelton, IV |
| 8,573,461 B2 | | 11/2013 | Shelton, IV et al. |
| 8,573,465 B2 | | 11/2013 | Shelton, IV |
| 8,602,288 B2 | | 12/2013 | Shelton, IV et al. |
| 8,616,431 B2 | | 12/2013 | Timm et al. |
| 8,783,541 B2 | | 7/2014 | Shelton, IV et al. |
| 8,800,838 B2 | | 8/2014 | Shelton, IV |
| 8,801,735 B2 | | 8/2014 | Shelton, IV et al. |
| 8,814,025 B2 | | 8/2014 | Miller et al. |
| 8,820,605 B2 | | 9/2014 | Shelton, IV |
| 8,844,789 B2 | | 9/2014 | Shelton, IV et al. |
| 8,899,464 B2 | | 12/2014 | Hueil et al. |
| 8,998,060 B2 | | 4/2015 | Bruewer et al. |
| 9,101,359 B2 | | 8/2015 | Smith et al. |
| 9,186,142 B2 | | 11/2015 | Fanelli et al. |
| 9,198,644 B2 | | 12/2015 | Balek et al. |
| 9,211,120 B2 | | 12/2015 | Scheib et al. |
| 9,301,759 B2 | | 4/2016 | Spivey et al. |
| 9,386,988 B2 | | 7/2016 | Baxter, III et al. |
| 9,393,018 B2 | | 7/2016 | Wang et al. |
| 9,398,911 B2 | | 7/2016 | Auld |
| 9,492,170 B2 | | 11/2016 | Bear et al. |
| 9,517,065 B2 | | 12/2016 | Simms et al. |
| 2006/0173470 A1 | * | 8/2006 | Oray ............... A61B 17/07207 |
| | | | 606/151 |
| 2008/0169328 A1 | | 7/2008 | Shelton, IV |
| 2009/0001122 A1 | * | 1/2009 | Prommersberger ........................ |
| | | | A61B 17/07207 |
| | | | 227/176.1 |
| 2012/0168487 A1 | * | 7/2012 | Holsten ............ A61B 17/00491 |
| | | | 227/176.1 |
| 2012/0241493 A1 | | 9/2012 | Baxter, III et al. |
| 2012/0241505 A1 | * | 9/2012 | Alexander, III ........................ |
| | | | A61B 17/00491 |
| | | | 227/179.1 |
| 2013/0062391 A1 | * | 3/2013 | Boudreaux ...... A61B 17/00491 |
| | | | 227/175.1 |
| 2013/0068816 A1 | | 3/2013 | Vasudevan et al. |
| 2013/0075447 A1 | | 3/2013 | Weisenburgh, II et al. |
| 2013/0206813 A1 | | 8/2013 | Nalagatla |
| 2013/0214030 A1 | | 8/2013 | Aronhalt et al. |
| 2014/0239036 A1 | | 8/2014 | Zerkle et al. |
| 2014/0239037 A1 | | 8/2014 | Boudreaux et al. |
| 2014/0239038 A1 | | 8/2014 | Leimbach et al. |
| 2014/0239040 A1 | | 8/2014 | Fanelli et al. |
| 2014/0239041 A1 | | 8/2014 | Zerkle et al. |
| 2014/0239043 A1 | | 8/2014 | Simms et al. |
| 2014/0239044 A1 | | 8/2014 | Hoffman |
| 2014/0263563 A1 | | 9/2014 | Stokes et al. |
| 2015/0272575 A1 | | 10/2015 | Leimbach et al. |
| 2015/0351754 A1 | | 12/2015 | Harris et al. |
| 2015/0351758 A1 | | 12/2015 | Shelton, IV et al. |
| 2015/0351763 A1 | | 12/2015 | Shelton, IV et al. |
| 2015/0374360 A1 | | 12/2015 | Scheib et al. |
| 2015/0374373 A1 | | 12/2015 | Rector et al. |
| 2016/0089146 A1 | | 3/2016 | Harris et al. |
| 2016/0278774 A1 | | 9/2016 | Shelton, IV et al. |

OTHER PUBLICATIONS

U.S. Appl. No. 14/827,856, filed Aug. 17, 2015.
U.S. Appl. No. 14/840,613, filed Aug. 31, 2015.
U.S. Appl. No. 14/871,071, filed Sep. 30, 2015.
U.S. Appl. No. 14/871,131, filed Sep. 30, 2015.
International Search Report and Written Opinion dated Jun. 12, 2017 for Application No. PCT/US2016/058403, 21 pgs.
Partial European Search Report and Written Opinion dated Feb. 16, 2017 for Application No. EP 16196332.7, 8 pgs.
European Search Report, Extended, and Written Opinion dated May 22, 2017 for Application No. EP 16196332.7, 14 pgs.

\* cited by examiner

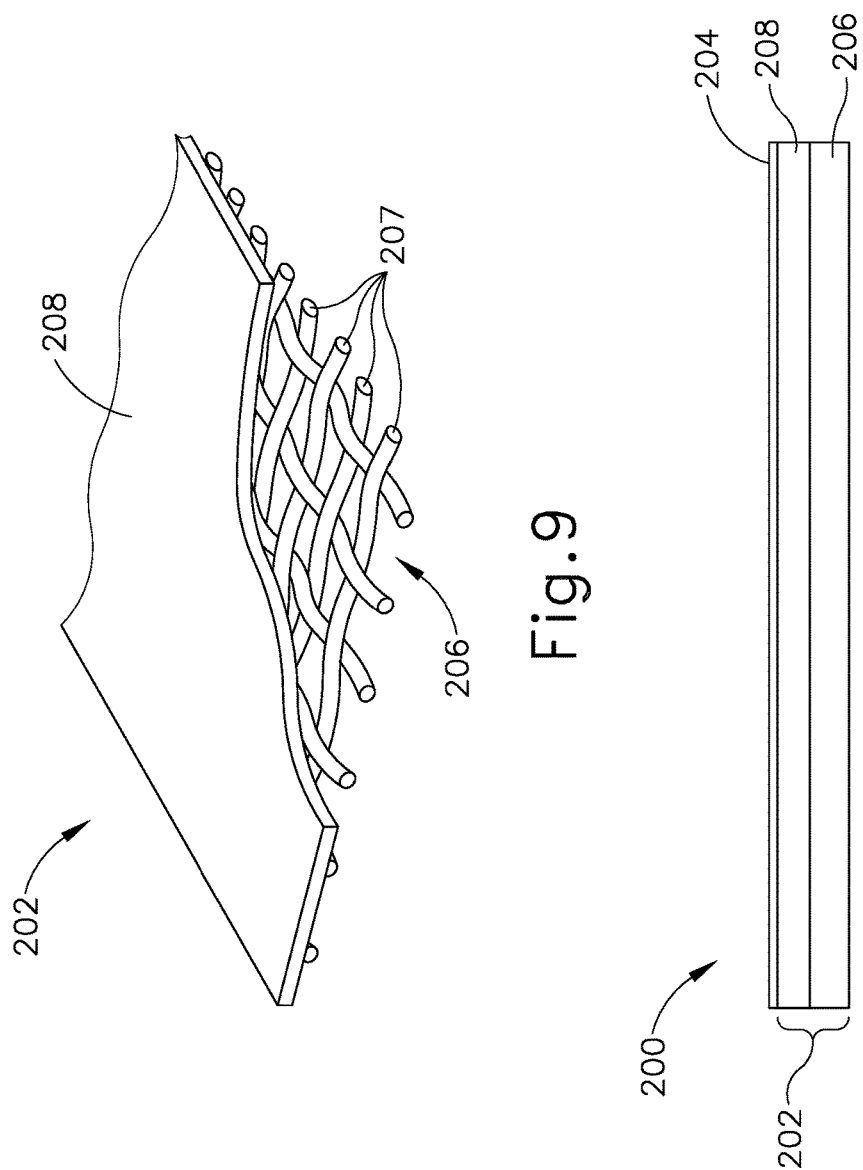

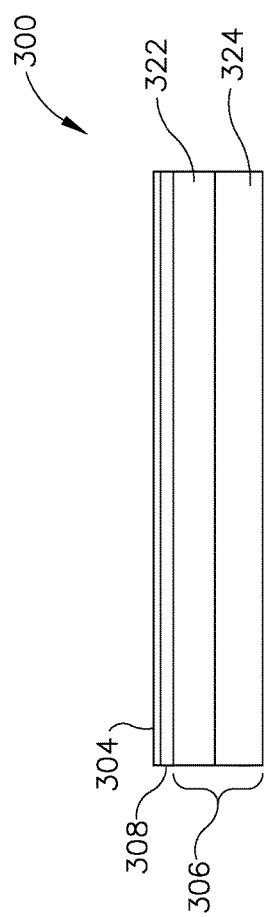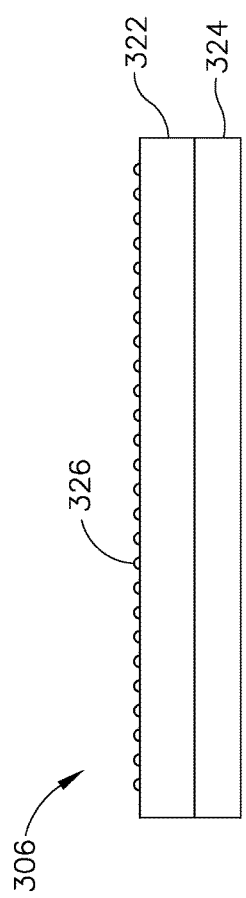

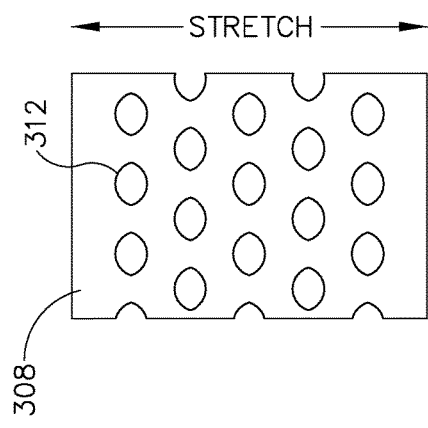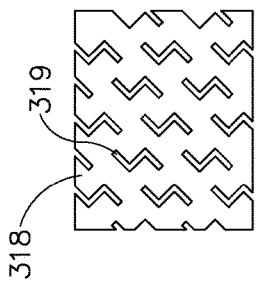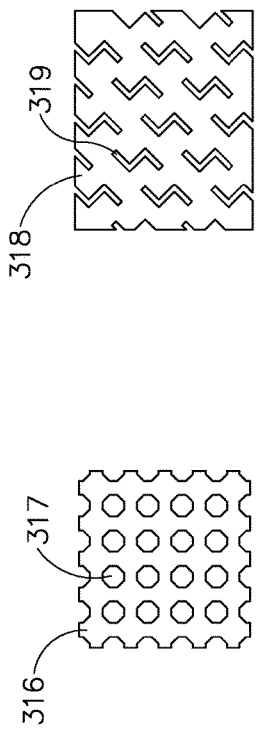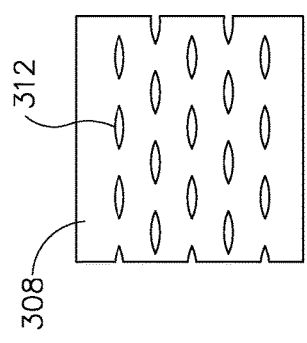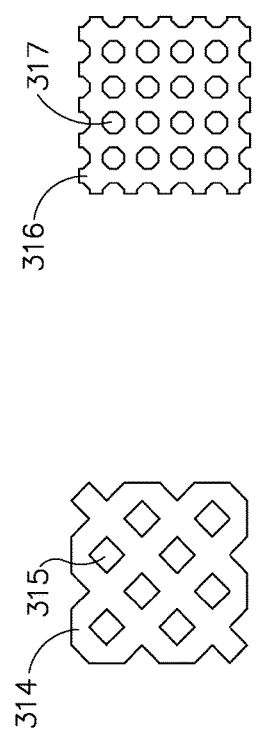

FLUID PENETRABLE BUTTRESS ASSEMBLY FOR A SURGICAL STAPLER

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasonic vibration, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. Patents is incorporated by reference herein.

While the surgical staplers referred to above are described as being used in endoscopic procedures, it should be understood that such surgical staplers may also be used in open procedures and/or other non-endoscopic procedures. By way of example only, a surgical stapler may be inserted through a thoracotomy, and thereby between a patient's ribs, to reach one or more organs in a thoracic surgical procedure that does not use a trocar as a conduit for the stapler. Such procedures may include the use of the stapler to sever and close a vessel leading to a lung. For instance, the vessels leading to an organ may be severed and closed by a stapler before removal of the organ from the thoracic cavity. Of course, surgical staplers may be used in various other settings and procedures.

Examples of surgical staplers that may be particularly suited for use through a thoracotomy are disclosed in U.S. Patent Pub. No. 2014/0243801, entitled "Surgical Instrument End Effector Articulation Drive with Pinion and Opposing Racks," published Aug. 28, 2014, issued as U.S. Pat. No. 9,186,142 on Nov. 17, 2015; U.S. Patent Pub. No. 2014/0239041, entitled "Lockout Feature for Movable Cutting Member of Surgical Instrument," published Aug. 28, 2014, issued as U.S. Pat. No. 9,717,497 on Aug. 1, 2017; U.S. Patent Pub. No. 2014/0239042, entitled "Integrated Tissue Positioning and Jaw Alignment Features for Surgical Stapler," published Aug. 28, 2014, issued as U.S. Pat. No. 9,517,065 on Dec. 13, 2016; U.S. Patent Pub. No. 2014/0239036, entitled "Jaw Closure Feature for End Effector of Surgical Instrument," published Aug. 28, 2014, issued as U.S. Pat. No. 9,839,421 on Dec. 12, 2017; U.S. Patent Pub. No. 2014/0239040, entitled "Surgical Instrument with Articulation Lock having a Detenting Binary Spring," published Aug. 28, 2014, issued as U.S. Pat. No. 9,867,615 on Jan. 16, 2018; U.S. Patent Pub. No. 2014/0239043, entitled "Distal Tip Features for End Effector of Surgical Instrument," published Aug. 28, 2014, issued as U.S. Pat. No. 9,622,746 on Apr. 18, 2017; U.S. Patent Pub. No. 2014/0239037, entitled "Staple Forming Features for Surgical Stapling Instrument," published Aug. 28, 2014, issued as U.S. Pat. No. 10,092,292 on Oct. 9, 2018; U.S. Patent Pub. No. 2014/0239038, entitled "Surgical Instrument with Multi-Diameter Shaft," published Aug. 28, 2014, issued as U.S. Pat. No. 9,795,379 on Oct. 24, 2017; and U.S. Patent Pub. No. 2014/0239044, entitled "Installation Features for Surgical Instrument End Effector Cartridge," published Aug. 28, 2014, issued as U.S. Pat. No. 9,808,248 on Nov. 7, 2017. The disclosure of each of the above-cited U.S. Patent Publications is incorporated by reference herein.

Additional surgical stapling instruments are disclosed in U.S. Pat. No. 8,801,735, entitled "Surgical Circular Stapler with Tissue Retention Arrangements," issued Aug. 12, 2014; U.S. Pat. No. 8,141,762, entitled "Surgical Stapler Comprising a Staple Pocket," issued Mar. 27, 2012; U.S. Pat. No. 8,371,491, entitled "Surgical End Effector Having Buttress Retention Features," issued Feb. 12, 2013; U.S. Pub. No. 2014/0263563, entitled "Method and Apparatus for Sealing End-to-End Anastomosis" published Sep. 18, 2014, issued as U.S. Pat. No. 9,597,082 on Mar. 21, 2017; U.S. Pub. No.

2014/0246473, entitled "Rotary Powered Surgical Instruments with Multiple Degrees of Freedom," published Sep. 4, 2014, issued as U.S. Pat. No. 9,398,911 on Jul. 26, 2016; U.S. Pub. No. 2013/0206813, entitled "Linear Stapler," published Aug. 15, 2013, now abandoned; U.S. Pub. No. 2008/0169328, entitled "Buttress Material for Use with a Surgical Stapler," published Jul. 17, 2008, now abandoned; U.S. patent application Ser. No. 14/300,804, entitled "Woven and Fibrous Materials for Reinforcing a Staple Line," filed Jun. 10, 2014, issued as U.S. Pat. No. 9,848,871 on Dec. 26, 2017; U.S. patent application Ser. No. 14/300,811, entitled "Devices and Methods for Sealing Staples in Tissue", issued as U.S. Pat. No. 9,936,954 on Apr. 10, 2018; and U.S. patent application Ser. No. 14/498,070, entitled "Radically Expandable Staple Line" filed Sep. 26, 2014, published as U.S. Pub. No. 2016/0089146 on Mar. 31, 2016. The disclosure of each of the above-cited U.S. Patents, U.S. Patent Publications, and U.S. Patent Applications is incorporated by reference herein.

In some instances, it may be desirable to equip a surgical stapling instrument with a buttress material to reinforce the mechanical fastening of tissue provided by staples. Such a buttress may prevent the applied staples from pulling through tissue and may otherwise reduce a risk of tissue tearing at or near the site of applied staples.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 9 depicts a partial perspective view of an exemplary multilayer buttress body, with a portion of a layer broken away to reveal another layer;

FIG. 10 depicts a side view of the multilayer buttress body of FIG. 9 combined with an adhesive layer to form a multilayer buttress assembly configured for use with the end effector of FIG. 2;

FIG. 11 depicts a side elevational view of another exemplary multilayer buttress assembly configured for use with the end effector of FIG. 2;

FIG. 12 depicts a side elevational view of the multilayer buttress assembly of FIG. 11 without an adhesive layer and without a film layer;

FIG. 14A depicts a top plan view of the film layer of the multilayer buttress of FIG. 11 in a relaxed position;

FIG. 14B depicts a top plan view of the film layer of the multilayer buttress of FIG. 11 in a stretched position;

FIG. 15 depicts a top plan view of an alternative example of a film layer that may be incorporated in the multilayer buttress of FIG. 11;

FIG. 16 depicts a top plan view of another alternative example of a film layer that may be incorporated in the multilayer buttress of FIG. 11;

FIG. 17 depicts a top plan view of another alternative example of a film layer that may be incorporated in the multilayer buttress of FIG. 11;

Figure 1:
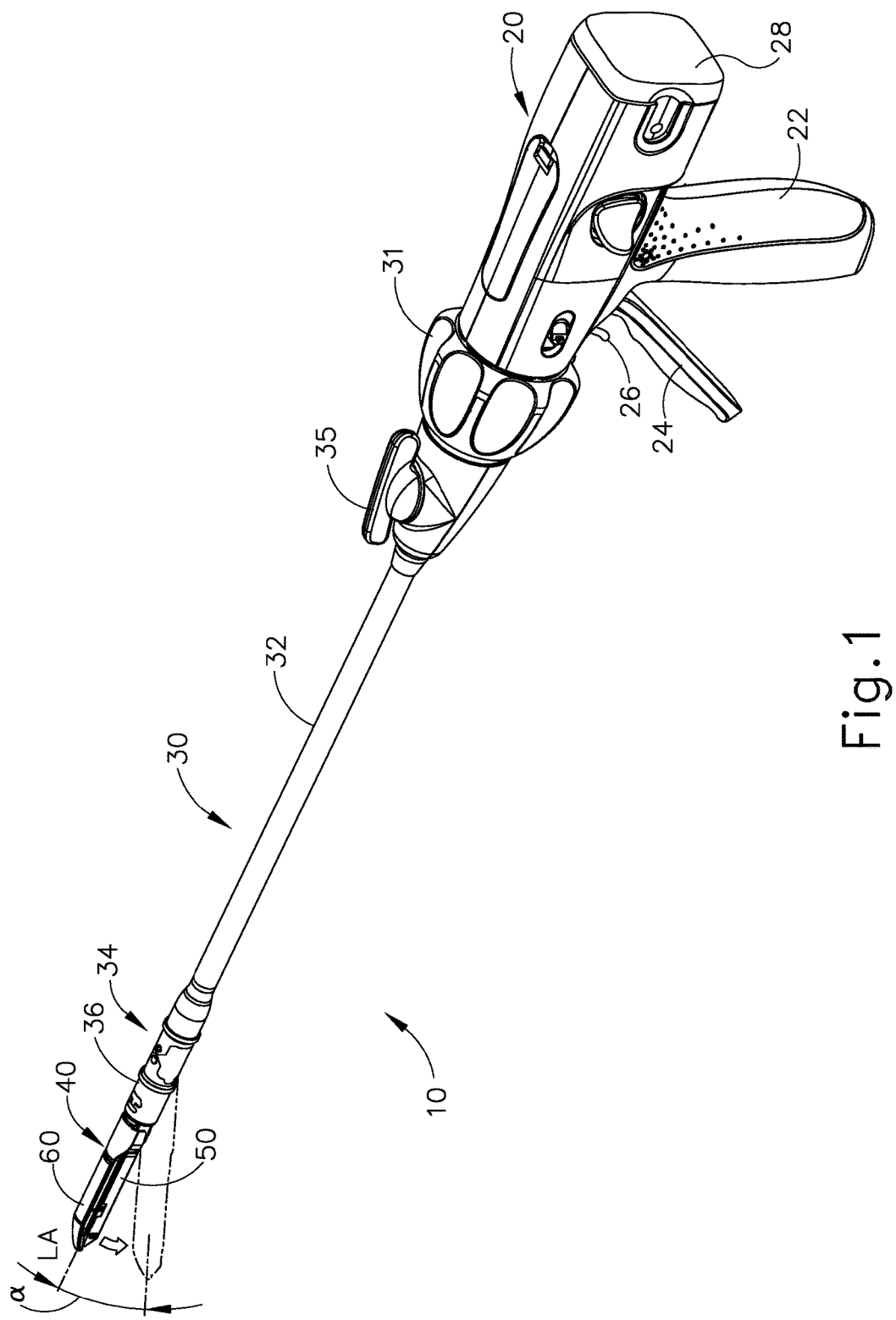
FIG. 1 depicts a perspective view of an exemplary articulating surgical stapling instrument.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Exemplary Surgical Stapler

FIG. 1 depicts an exemplary surgical stapling and severing instrument (10) that includes a handle assembly (20), a shaft assembly (30), and an end effector (40). End effector (40) and the distal portion of shaft assembly (30) are sized for insertion, in a nonarticulated state as depicted in FIG. 1, through a trocar cannula to a surgical site in a patient for performing a surgical procedure. By way of example only, such a trocar may be inserted in a patient's abdomen, between two of the patient's ribs, or elsewhere. In some settings, instrument (10) is used without a trocar. For instance, end effector (40) and the distal portion of shaft assembly (30) may be inserted directly through a thoracotomy or other type of incision. It should be understood that terms such as "proximal" and "distal" are used herein with reference to a clinician gripping handle assembly (20) of instrument (10). Thus, end effector (40) is distal with respect to the more proximal handle assembly (20). It will be further appreciated that for convenience and clarity, spatial terms such as "vertical" and "horizontal" are used herein with respect to the drawings. However, surgical instruments are used in many orientations and positions, and these terms are not intended to be limiting and absolute.

A. Exemplary Handle Assembly and Shaft Assembly

As shown in FIG. 1, handle assembly (20) of the present example comprises pistol grip (22), a closure trigger (24), and a firing trigger (26). Each trigger (24, 26) is selectively pivotable toward and away from pistol grip (22) as will be described in greater detail below. Handle assembly (20) further includes a removable battery pack (28). These components will also be described in greater detail below. Of course, handle assembly (20) may have a variety of other components, features, and operabilities, in addition to or in lieu of any of those noted above. Other suitable configurations for handle assembly (20) will be apparent to those of ordinary skill in the art in view of the teachings herein.

Figure 2:
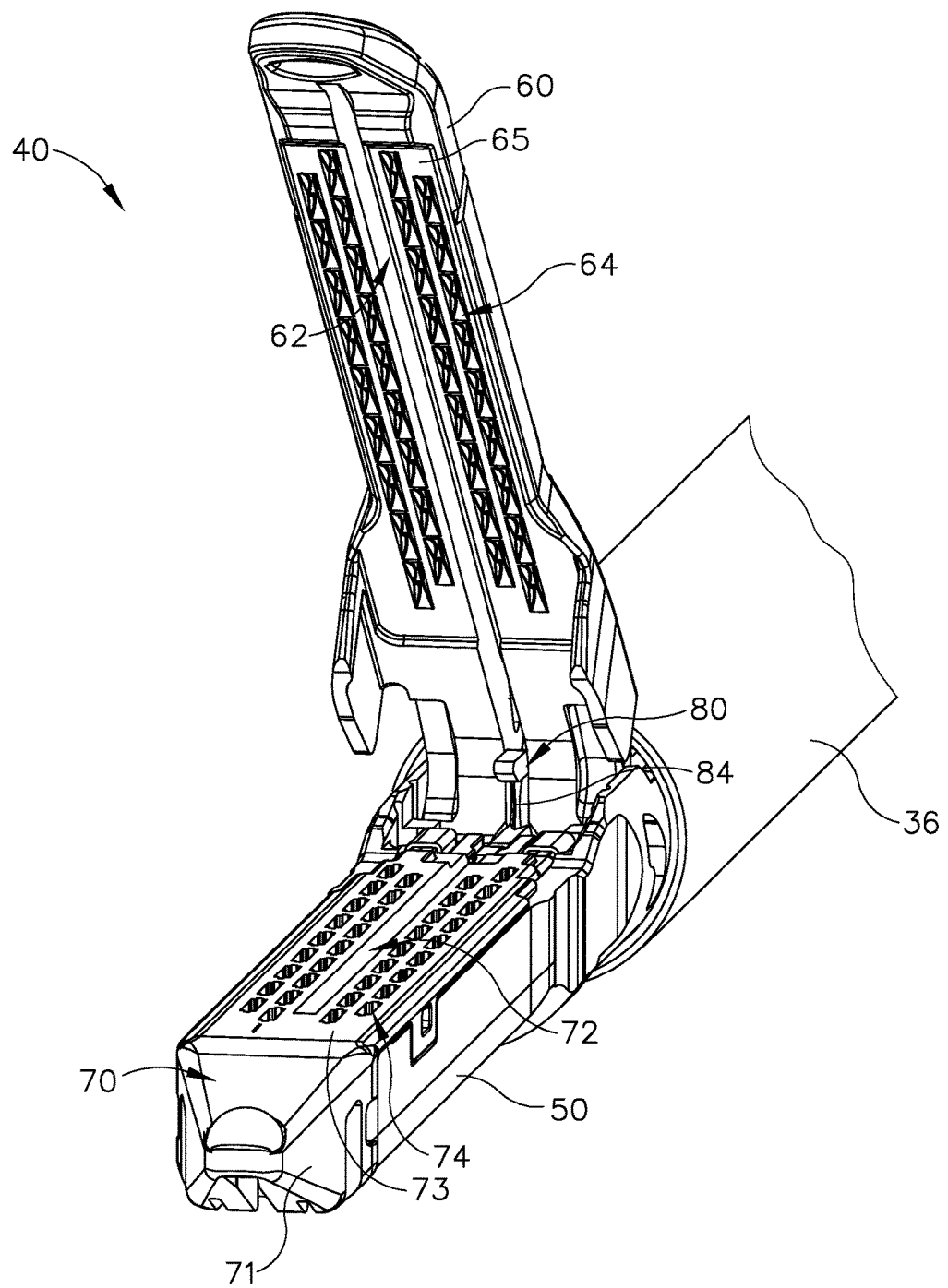
FIG. 2 depicts a perspective view of an end effector of the instrument of FIG. 1, with the end effector in an open configuration.

As shown in FIGS. 1-2, shaft assembly (30) of the present example comprises an outer closure tube (32), an articulation section (34), and a closure ring (36), which is further coupled with end effector (40). Closure tube (32) extends along the length of shaft assembly (30). Closure ring (36) is positioned distal to articulation section (34). Closure tube (32) and closure ring (36) are configured to translate longitudinally relative to handle assembly (20). Longitudinal translation of closure tube (32) is communicated to closure ring (36) via articulation section (34). Exemplary features that may be used to provide longitudinal translation of closure tube (32) and closure ring (36) will be described in greater detail below.

Articulation section (34) is operable to laterally deflect closure ring (36) and end effector (40) laterally away from the longitudinal axis (LA) of shaft assembly (30) at a desired angle (a). In the present example, articulation is controlled through an articulation control knob (35) which is located at the proximal end of shaft assembly (30). Closure ring (36) and end effector (40) pivot about an axis that is perpendicular to the longitudinal axis (LA) of shaft assembly (30) in response to rotation of knob (35). Articulation section (34) is configured to communicate longitudinal translation of closure tube (32) to closure ring (36), regardless of whether articulation section (34) is in a straight configuration or an articulated configuration. By way of example only, articulation section (34) and/or articulation control knob (35) may be constructed and operable in accordance with at least some of the teachings of U.S. Pub. No. 2014/0243801, entitled "Surgical Instrument End Effector Articulation Drive with Pinion and Opposing Racks," published Aug. 28, 2014, issued as U.S. Pat. No. 9,186,142 on Nov. 17, 2015, the disclosure of which is incorporated by reference herein; and/or U.S. patent application Ser. No. 14/314,125, entitled "Articulation Drive Features for Surgical Stapler," filed Jun. 25, 2014, published as U.S. Pub. No. 2015/0374360 on Dec. 31, 2015, the disclosure of which is incorporated by reference herein; and/or in accordance with the various teachings below. Other suitable forms that articulation section (34) and articulation knob (35) may take will be apparent to those of ordinary skill in the art in view of the teachings herein.

As shown in FIG. 1, shaft assembly (30) of the present example further includes a rotation knob (31). Rotation knob (31) is operable to rotate the entire shaft assembly (30) and end effector (40) relative to handle assembly (20) about the longitudinal axis (LA) of shaft assembly (30). Of course, shaft assembly (30) may have a variety of other components, features, and operabilities, in addition to or in lieu of any of those noted above. By way of example only, at least part of shaft assembly (30) is constructed in accordance with at least some of the teachings of U.S. Pub. No. 2014/0239038, entitled "Surgical Instrument with Multi-Diameter Shaft," published Aug. 28, 2014, issued as U.S. Pat. No. 9,795,379 on Oct. 24, 2017, the disclosure of which is incorporated by reference herein. Other suitable configurations for shaft assembly (30) will be apparent to those of ordinary skill in the art in view of the teachings herein.

B. Exemplary End Effector

Figure 3:
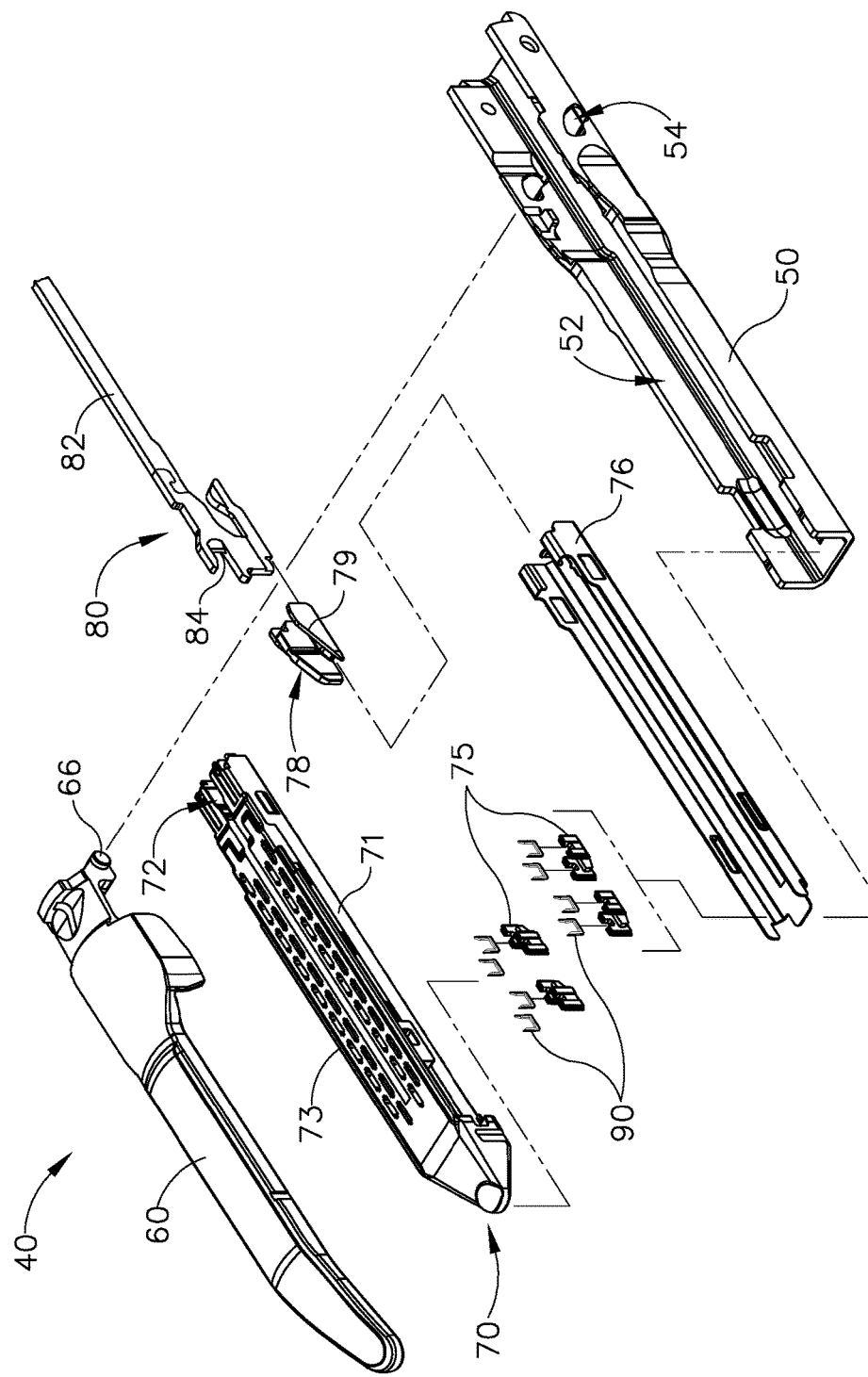
FIG. 3 depicts an exploded perspective view of the end effector of FIG. 2.

As also shown in FIGS. 1-3, end effector (40) of the present example includes a lower jaw (50) and a pivotable anvil (60). Anvil (60) includes a pair of integral, outwardly extending pins (66) that are disposed in corresponding curved slots (54) of lower jaw (50). Anvil (60) is pivotable toward and away from lower jaw (50) between an open position (shown in FIG. 2) and a closed position (shown in FIG. 1). Use of the term "pivotable" (and similar terms with "pivot" as a base) should not be read as necessarily requiring pivotal movement about a fixed axis. For instance, in the present example, anvil (60) pivots about an axis that is defined by pins (66), which slide along curved slots (54) of lower jaw (50) as anvil (60) moves toward lower jaw (50). In such versions, the pivot axis translates along the path defined by slots (54) while anvil (60) simultaneously pivots about that axis. In addition or in the alternative, the pivot axis may slide along slots (54) first, with anvil (60) then pivoting about the pivot axis after the pivot axis has slid a certain distance along the slots (54). It should be understood that such sliding/translating pivotal movement is encompassed within terms such as "pivot," "pivots," "pivotal," "pivotable," "pivoting," and the like. Of course, some versions may provide pivotal movement of anvil (60) about an axis that remains fixed and does not translate within a slot or channel, etc.

As best seen in FIG. 3, lower jaw (50) of the present example defines a channel (52) that is configured to receive a staple cartridge (70). Staple cartridge (70) may be inserted into channel (52), end effector (40) may be actuated, and then staple cartridge (70) may be removed and replaced with another staple cartridge (70). Lower jaw (50) thus releasably retains staple cartridge (70) in alignment with anvil (60) for actuation of end effector (40). In some versions, lower jaw (50) is constructed in accordance with at least some of the teachings of U.S. Pub. No. 2014/0239044, entitled "Installation Features for Surgical Instrument End Effector Cartridge," published Aug. 28, 2014, issued as U.S. Pat. No.

9,808,248 on Nov. 7, 2017, the disclosure of which is incorporated by reference herein. Other suitable forms that lower jaw (50) may take will be apparent to those of ordinary skill in the art in view of the teachings herein.

As best seen in FIGS. 2-3, staple cartridge (70) of the present example comprises a cartridge body (71) and a tray (76) secured to the underside of cartridge body (71). The upper side of cartridge body (71) presents a deck (73), against which tissue may be compressed when anvil (60) is in a closed position. Cartridge body (71) further defines a longitudinally extending channel (72) and a plurality of staple pockets (74). A staple (90) is positioned in each staple pocket (74). A staple driver (75) is also positioned in each staple pocket (74), underneath a corresponding staple (90), and above tray (76). As will be described in greater detail below, staple drivers (75) are operable to translate upwardly in staple pockets (74) to thereby drive staples (90) upwardly through staple pockets (74) and into engagement with anvil (60). Staple drivers (75) are driven upwardly by a wedge sled (78), which is captured between cartridge body (71) and tray (76), and which translates longitudinally through cartridge body (71).

Wedge sled (78) includes a pair of obliquely angled cam surfaces (79), which are configured to engage staple drivers (75) and thereby drive staple drivers (75) upwardly as wedge sled (78) translates longitudinally through cartridge (70). For instance, when wedge sled (78) is in a proximal position, staple drivers (75) are in downward positions and staples (90) are located in staple pockets (74). As wedge sled (78) is driven to the distal position by a translating knife member (80), wedge sled (78) drives staple drivers (75) upwardly, thereby driving staples (90) out of staple pockets (74) and into staple forming pockets (64) that are formed in the underside (65) of anvil (60). Thus, staple drivers (75) translate along a vertical dimension as wedge sled (78) translates along a horizontal dimension.

In some versions, staple cartridge (70) is constructed and operable in accordance with at least some of the teachings of U. U.S. Pub. No. 2014/0239042, entitled "Integrated Tissue Positioning and Jaw Alignment Features for Surgical Stapler," published Aug. 28, 2014, issued as U.S. Pat. No. 9,517,065 on Dec. 13, 2016, the disclosure of which is incorporated by reference herein. In addition or in the alternative, staple cartridge (70) may be constructed and operable in accordance with at least some of the teachings of U.S. Pub. No. 2014/0239044, entitled "Installation Features for Surgical Instrument End Effector Cartridge," published Aug. 28, 2014, issued as U.S. Pat. No. 9,808,248 on Nov. 7, 2017, the disclosure of which is incorporated by reference herein. Other suitable forms that staple cartridge (70) may take will be apparent to those of ordinary skill in the art in view of the teachings herein.

As best seen in FIG. 2, anvil (60) of the present example comprises a longitudinally extending channel (62) and a plurality of staple forming pockets (64). Channel (62) is configured to align with channel (72) of staple cartridge (70) when anvil (60) is in a closed position. Each staple forming pocket (64) is positioned to lie over a corresponding staple pocket (74) of staple cartridge (70) when anvil (60) is in a closed position. Staple forming pockets (64) are configured to deform the legs of staples (90) when staples (90) are driven through tissue and into anvil (60). In particular, staple forming pockets (64) are configured to bend the legs of staples (90) to secure the formed staples (90) in the tissue. Anvil (60) may be constructed in accordance with at least some of the teachings of U.S. Pub. No. 2014/0239042, entitled "Integrated Tissue Positioning and Jaw Alignment Features for Surgical Stapler," published Aug. 28, 2014, issued as U.S. Pat. No. 9,517,065 on Dec. 13, 2016; at least some of the teachings of U.S. Pub. No. 2014/0239036, entitled "Jaw Closure Feature for End Effector of Surgical Instrument," published Aug. 28, 2014, issued as U.S. Pat. No. 9,839,421 on Dec. 12, 2017; and/or at least some of the teachings of U.S. Pub. No. 2014/0239037, entitled "Staple Forming Features for Surgical Stapling Instrument," published Aug. 28, 2014, issued as U.S. Pat. No. 10,092,292 on Oct. 9, 2018, the disclosure of which is incorporated by reference herein. Other suitable forms that anvil (60) may take will be apparent to those of ordinary skill in the art in view of the teachings herein.

In the present example, a knife member (80) is configured to translate through end effector (40). As best seen in FIG. 3, knife member (80) is secured to the distal end of a firing beam (82), which extends through a portion of shaft assembly (30). As best seen in FIG. 2, knife member (80) is positioned in channels (62, 72) of anvil (60) and staple cartridge (70). Knife member (80) includes a distally presented cutting edge (84) that is configured to sever tissue that is compressed between anvil (60) and deck (73) of staple cartridge (70) as knife member (80) translates distally through end effector (40). As noted above, knife member (80) also drives wedge sled (78) distally as knife member (80) translates distally through end effector (40), thereby driving staples (90) through tissue and against anvil (60) into formation.

C. Exemplary Actuation of End Effector

In the present example, anvil (60) is driven toward lower jaw (50) by advancing closure ring (36) distally relative to end effector (40). Closure ring (36) cooperates with anvil (60) through a camming action to drive anvil (60) toward lower jaw (50) in response to distal translation of closure ring (36) relative to end effector (40). Similarly, closure ring (36) may cooperate with anvil (60) to open anvil (60) away from lower jaw (50) in response to proximal translation of closure ring (36) relative to end effector (40). By way of example only, closure ring (36) and anvil (60) may interact in accordance with at least some of the teachings of U.S. Pub. No. 2014/0239036, entitled "Jaw Closure Feature for End Effector of Surgical Instrument," published Aug. 28, 2014, issued as U.S. Pat. No. 9,839,421 on Dec. 12, 2017, the disclosure of which is incorporated by reference herein; and/or in accordance with at least some of the teachings of U.S. patent application Ser. No. 14/314,108, entitled "Jaw Opening Feature for Surgical Stapler," filed on Jun. 25, 2014, published as U.S. Pub. No. 2015/0374373 on Dec. 31, 2015, the disclosure of which is incorporated by reference herein.

As noted above, handle assembly (20) includes a pistol grip (22) and a closure trigger (24). As also noted above, anvil (60) is closed toward lower jaw (50) in response to distal advancement of closure ring (36). In the present example, closure trigger (24) is pivotable toward pistol grip (22) to drive closure tube (32) and closure ring (36) distally. Various suitable components that may be used to convert pivotal movement of closure trigger (24) toward pistol grip (22) into distal translation of closure tube (32) and closure ring (36) relative to handle assembly (20) will be apparent to those of ordinary skill in the art in view of the teachings herein.

Also in the present example, instrument (10) provides motorized control of firing beam (82). In particular, instrument (10) includes motorized components that are configured to drive firing beam (82) distally in response to pivoting of firing trigger (26) toward pistol grip (22). In some versions, a motor (not shown) is contained in pistol grip (22) and receives power from battery pack (28). This motor is coupled with a transmission assembly (not shown) that converts rotary motion of a drive shaft of the motor into linear translation of firing beam (82). By way of example only, the features that are operable to provide motorized actuation of firing beam (82) may be configured and operable in accordance with at least some of the teachings of U.S. Pat. No. 8,210,411, entitled "Motor-Driven Surgical Instrument," issued Jul. 3, 2012, the disclosure of which is incorporated by reference herein.; U.S. Pat. No. 8,453,914, entitled "Motor-Driven Surgical Cutting Instrument with Electric Actuator Directional Control Assembly," issued Jun. 4, 2013, the disclosure of which is incorporated by reference herein; and/or U.S. patent application Ser. No. 14/226,142, entitled "Surgical Instrument Comprising a Sensor System," filed Mar. 26, 2014, issued as U.S. Pat. No. 9,913,642 on Mar. 13, 2018, the disclosure of which is incorporated by reference herein.

It should also be understood that any other components or features of instrument (10) may be configured and operable in accordance with any of the various references cited herein. Additional exemplary modifications that may be provided for instrument (10) will be described in greater detail below. Various suitable ways in which the below teachings may be incorporated into instrument (10) will be apparent to those of ordinary skill in the art. Similarly, various suitable ways in which the below teachings may be combined with various teachings of the references cited herein will be apparent to those of ordinary skill in the art. It should therefore be understood that the teachings below may be readily incorporated into the various instruments taught in the various references that are cited herein. It should also be understood that the below teachings are not limited to instrument (10) or devices taught in the references cited herein. The below teachings may be readily applied to various other kinds of instruments, including instruments that would not be classified as surgical staplers. Various other suitable devices and settings in which the below teachings may be applied will be apparent to those of ordinary skill in the art in view of the teachings herein.

II. Exemplary Buttress Assembly for Surgical Stapler

In some instances, it may be desirable to equip end effector (40) with a buttress material to reinforce the mechanical fastening of tissue provided by staples (90). Such a buttress may prevent the applied staples (90) from pulling through the tissue and may otherwise reduce a risk of tissue tearing at or near the site of applied staples (90). In addition to or as an alternative to providing structural support and integrity to a line of staples (90), a buttress may provide various other kinds of effects such as spacing or gap-filling, administration of therapeutic agents, and/or other effects. In some instances, a buttress may be provided on deck (73) of staple cartridge (70). In some other instances, a buttress may be provided on the surface of anvil (60) that faces staple cartridge (70). It should also be understood that a first buttress may be provided on deck (73) of staple cartridge (70) while a second buttress is provided on anvil (60) of the same end effector (40). Various examples of forms that a buttress may take will be described in greater detail below. Various ways in which a buttress may be secured to a staple cartridge (70) or an anvil (60) will also be described in greater detail below.

A. Exemplary Composition of Buttress Assembly for Surgical Stapler

Figure 4:
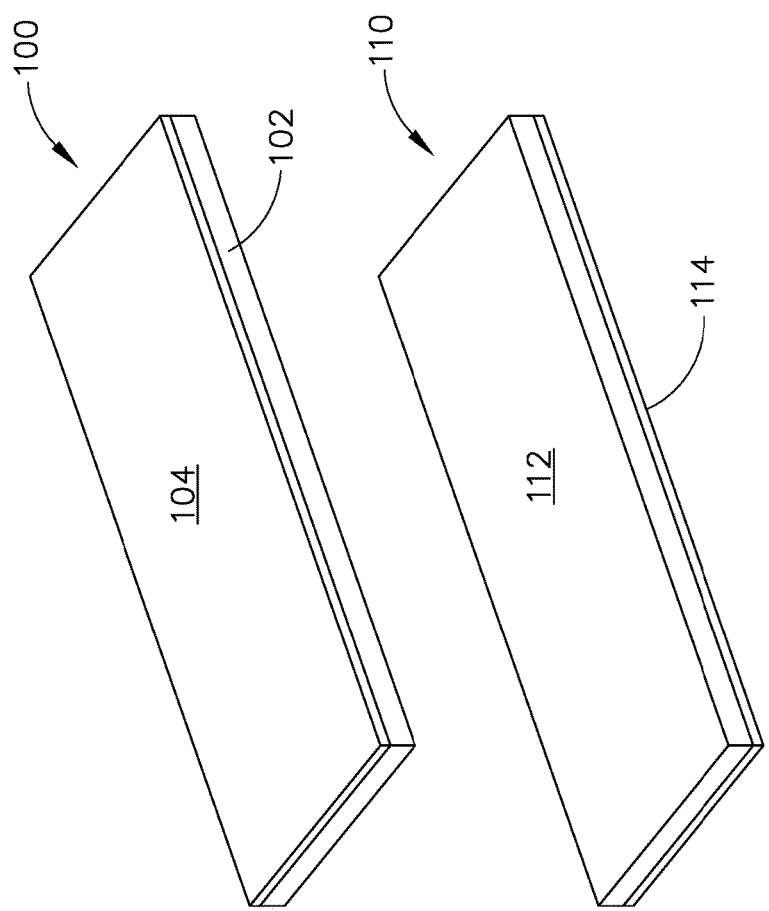
FIG. 4 depicts a perspective view of an exemplary upper buttress and an exemplary lower buttress, each of which may be applied to the end effector of FIG. 2.

FIG. 4 shows an exemplary pair of buttress assemblies (100, 110) with a basic composition. Buttress assembly (100) of this example comprises a buttress body (102) and an upper adhesive layer (104). Similarly, buttress assembly (110) comprises a buttress body (112) and a lower adhesive layer (114). In the present example, each buttress body (102, 112) comprises a strong yet flexible material configured to structurally support a line of staples (90). By way of example only, each buttress body (102, 112) may comprise a woven mesh of polyglactin 910 material by Ethicon, Inc. of Somerville, N.J. Alternatively, any other suitable materials or combinations of materials may be used in addition to or as an alternative to polyglactin 910 material to form each buttress body (102, 112). Each buttress body (102, 112) may take any other suitable form and may be constructed of any other suitable material(s). By way of further example only, each buttress body (102, 112) may comprise one or more of the following: NEOVEIL absorbable PGA felt by Gunze Limited, of Kyoto, Japan; SEAMGUARD polyglycolic acid:trimethylene carbonate (PGA:TMC) reinforcement material by W.L. Gore & Associates, Inc., of Flagstaff, Ariz.; PERI-STRIPS DRY with VERITAS Collagen Matrix (PSDV) reinforcement material, by Baxter Healthcare Corporation of Deerfield, Ill.; BIODESIGN biologic graft material by Cook Medical, Bloomington, Ind.; and/or SURGICEL NU-KNIT hemostat material by Ethicon, Inc. of Somerville, N.J. Still other suitable materials that may be used to form each buttress body (102, 112) will be apparent to those of ordinary skill in the art in view of the teachings herein.

In addition, or in the alternative, each buttress body (102, 112) may comprise a material including, for example, a hemostatic agent such as fibrin to assist in coagulating blood and reduce bleeding at the severed and/or stapled surgical site along tissue (90). As another merely illustrative example, each buttress body (102, 112) may comprise other adjuncts or hemostatic agents such as thrombin may be used such that each buttress body (102, 112) may assist to coagulate blood and reduce the amount of bleeding at the surgical site. Other adjuncts or reagents that may be incorporated into each buttress body (102, 112) may further include but are not limited to medical fluid or matrix components. Merely illustrative examples of materials that may be used to form each buttress body (102, 112), as well as materials that may be otherwise incorporated into each buttress body (102, 112), are disclosed in U.S. patent application Ser. No. 14/667,842, entitled "Method of Applying a Buttress to a Surgical Stapler," filed Mar. 25, 2015, published as U.S. Pub. No. 2016/0278774 on Sep. 29, 2016, the disclosure of which is incorporated by reference herein. Alternatively, any other suitable materials may be used.

By way of further example only, each buttress body (102, 112) may be constructed in accordance with at least some of the teachings of U.S. Patent Pub. No. 2012/0241493, entitled "Tissue Thickness Compensator Comprising Controlled Release and Expansion," published Sep. 27, 2012, issued as U.S. Pat. No. 10,123,798 on Nov. 13, 2018, the disclosure of which is incorporated by reference herein; U.S. Patent Pub. No. 2013/0068816, entitled "Surgical Instrument and Buttress Material," published Mar. 21, 2013, now abandoned, the disclosure of which is incorporated by reference herein; U.S. Patent Pub. No. 2013/0062391, entitled "Surgical Instrument with Fluid Fillable Buttress," published Mar. 14, 2013, issued as U.S. Pat. No. 9,999,408 on Jun. 19, 2018, the disclosure of which is incorporated by reference herein; U.S. Patent Pub. No. 2013/0068820, entitled "Fibrin Pad Matrix with Suspended Heat Activated Beads of Adhesive," published Mar. 21, 2013, issued as U.S. Pat. No. 8,814,025 on Aug. 26, 2014, the disclosure of which is incorporated by reference herein; U.S. Patent Pub. No. 2013/0082086, entitled "Attachment of Surgical Staple Buttress to Cartridge," published Apr. 4, 2013, issued as U.S. Pat. No. 8,899,464 on Dec. 2, 2014, the disclosure of which is incorporated by reference herein; U.S. Patent Pub. No. 2013/0037596, entitled "Device for Applying Adjunct in Endoscopic Procedure," published Feb. 14, 2013, issued as U.S. Pat. No. 9,492,170, the disclosure of which is incorporated by reference herein; U.S. Patent Pub. No. 2013/0062393, entitled "Resistive Heated Surgical Staple Cartridge with Phase Change Sealant," published Mar. 14, 2013, issued as U.S. Pat. No. 8,998,060 on Apr. 7, 2015, the disclosure of which is incorporated by reference herein; U.S. Patent Pub. No. 2013/0075446, entitled "Surgical Staple Assembly with Hemostatic Feature," published Mar. 28, 2013, issued as U.S. Pat. No. 9,393,018 on Jul. 19, 2016, the disclosure of which is incorporated by reference herein; U.S. Patent Pub. No. 2013/0062394, entitled "Surgical Staple Cartridge with Self-Dispensing Staple Buttress," published Mar. 14, 2013, issued as U.S. Pat. No. 9,101,359 on Aug. 11, 2015, the disclosure of which is incorporated by reference herein; U.S. Patent Pub. No. 2013/0075445, entitled "Anvil Cartridge for Surgical Fastening Device," published Mar. 28, 2013, issued as U.S Pat. No. 9,198,644 on Dec. 1, 2015, the disclosure of which is incorporated by reference herein; U.S. Patent Pub. No. 2013/0075447, entitled "Adjunct Therapy for Applying Hemostatic Agent," published Mar. 28, 2013, now abandoned, the disclosure of which is incorporated by reference herein; U.S. Patent Pub. No. 2013/0256367, entitled "Tissue Thickness Compensator Comprising a Plurality of Medicaments," published Oct. 3, 2013, issued as U.S. Pat. No. 9,211,120 on Dec. 15, 2015, the disclosure of which is incorporated by reference herein; U.S. patent application Ser. No. 14/300,954, entitled "Adjunct Materials and Methods of Using Same in Surgical Methods for Tissue Sealing," filed Jun. 10, 2014, published as U.S. Pub. No. 2015/0351758 on Dec. 10, 2015, the disclosure of which is incorporated by reference herein; U.S. patent applicatio Ser. No. 14/827,856, entitled "Implantable Layers for a Surgical Instrument," filed Aug. 17, 2015, published as U.S. Pub. No. 2017/0049444 on Feb. 23, 2017, the disclosure of which is incorporated by reference herein; U.S. patent application Ser. No. 14/840,613, entitled "Drug Eluting Adjuncts and Methods of Using Drug Eluting Adjuncts," filed Aug. 31, 2015, published as U.S. Pub. No. 2017/0055486 on Mar. 2, 2017, the disclosure of which is incorporated by reference herein; U.S. patent application Ser. No. 14/871,071, entitled "Compressible Adjunct with Crossing Spacer Fibers," filed Sep. 30, 2015, published as U.S. Pub. No. 2017/0086837 on Mar. 30, 2017, the disclosure of which is incorporated by reference herein; and/or U.S. patent applicaton Ser. No. 14/871,131, published as U.S. Pub. No. 2017/0086842 on Mar. 30, 2017, entitled "Method for Applying an Implantable Layer to a Fastener Cartridge," filed Sep. 30, 2015, the disclosure of which is incorporated by reference herein.

In the present example, adhesive layer (104) is provided on buttress body (102) in order to adhere buttress body (102) to underside (65) of anvil (60). Similarly, adhesive layer (114) is provided on buttress body (112) in order to adhere buttress body (112) to deck (73) of staple cartridge (70). Adherence of the buttress body (102) to underside (65) of anvil (60) or to deck (73) of staple cartridge (70) can occur through a variety of mechanisms including but not limited to a pressure sensitive adhesive. In some versions, each adhesive layer (104, 114) comprise a pressure sensitive adhesive material. Examples of various suitable materials that may be used to form adhesive layers (104, 114) are disclosed in U.S. patent application Ser. No. 14/667,842, entitled "Method of Applying a Buttress to a Surgical Stapler," filed Mar. 25, 2015, published as U.S. Pub. No. 2016/0278774 on Sep. 29, 2016, the disclosure of which is incorporated by reference herein. Alternatively, any other suitable materials may be used. It should be understood that the term "adhesive," as used herein, may include (but is not limited to) tacky materials and also materials that are pliable or wax-like and adhere to a complex geometry via deformation and conformance. Some suitable adhesives may provide such pliability to adhere to a complex geometry via deformation and conformance without necessarily providing a high initial tack. In some instances, adhesives with lower tackiness may be removed more cleanly from surfaces. Various suitable materials that may be used to form adhesive layers (104, 114) will be apparent to those of ordinary skill in the art in view of the teachings herein.

B. Exemplary Materials and Techniques for Providing Adhesion of Buttress to Surgical Stapler As noted above, a buttress assembly (100, 110) may include a layer (104, 114) of adhesive material (or other form of adhesive material) that adheres buttress body (102, 112) to either underside (65) of anvil (60) or deck (73) of staple cartridge (70). Such an adhesive material may provide proper positioning of buttress body (102, 112) before and during actuation of end effector (40); then allow buttress body (102, 112) to separate from end effector (40) after end effector (40) has been actuated, without causing damage to buttress body (102, 112) that is substantial enough to compromise the proper subsequent functioning of buttress body (102, 112).

Figure 5:
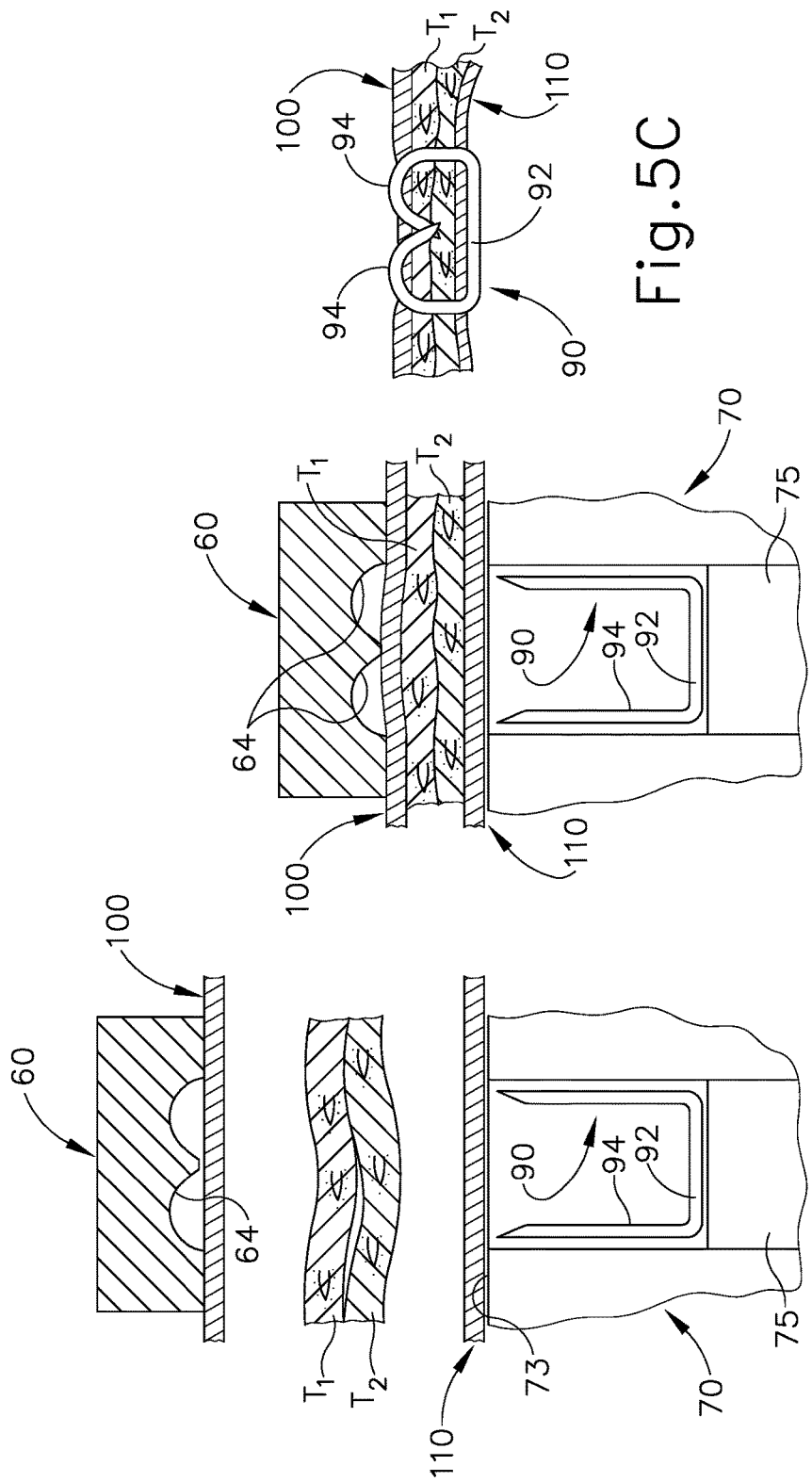
FIG. 5A depicts a cross-sectional end view of a portion of the end effector of FIG. 2 with a buttress assembly formed by the buttresses of FIG. 4 applied to the end effector, with tissue positioned between the buttresses in the end effector, and with the anvil in an open position.
FIG. 5B depicts a cross-sectional end view of the combined end effector and buttress assembly of FIG. 5A, with tissue positioned between the buttresses in the end effector, and with the anvil in a closed position.
FIG. 5C depicts a cross-sectional view of a staple and the buttress assembly of FIG. 5A having been secured to the tissue by the end effector of FIG. 2.

FIGS. 5A-5C show a sequence where an end effector (40) that has been loaded with buttress assemblies (100, 110) is actuated to drive staples (90) through two apposed layers of tissue ($T_1$, $T_2$), with buttress assemblies (100, 110) being secured to the same layers of tissue ($T_1$, $T_2$) by staples (90). In particular, FIG. 5A shows layers of tissue ($T_1$, $T_2$) positioned between anvil (60) and staple cartridge (70), with anvil (60) in the open position. Buttress assembly (100) is adhered to the underside (65) of anvil (60) via adhesive layer (104); while buttress assembly (110) is adhered to deck (73) of staple cartridge (70) via adhesive layer (114). Layers of tissue ($T_1$, $T_2$) are thus interposed between buttress assemblies (100, 110). Next, trigger (24) is pivoted toward pistol grip (22) to drive closure tube (32) and closure ring (36) distally. This drives anvil (60) to the closed position as shown in FIG. 5B. At this stage, layers of tissue ($T_1$, $T_2$) are compressed between anvil (60) and staple cartridge (70), with buttress assemblies (100, 110) engaging opposite surfaces of tissue layers ($T_1$, $T_2$). End effector (40) is then actuated as described above, driving staple (90) through buttress assemblies (100, 110) and tissue (90). As shown in FIG. 5C, crown (92) of driven staple (90) captures and retains buttress assembly (110) against layer of tissue ($T_2$). Deformed legs (94) of staple (90) capture and retain buttress assembly (100) against layer of tissue ($T_1$).

Figure 6:
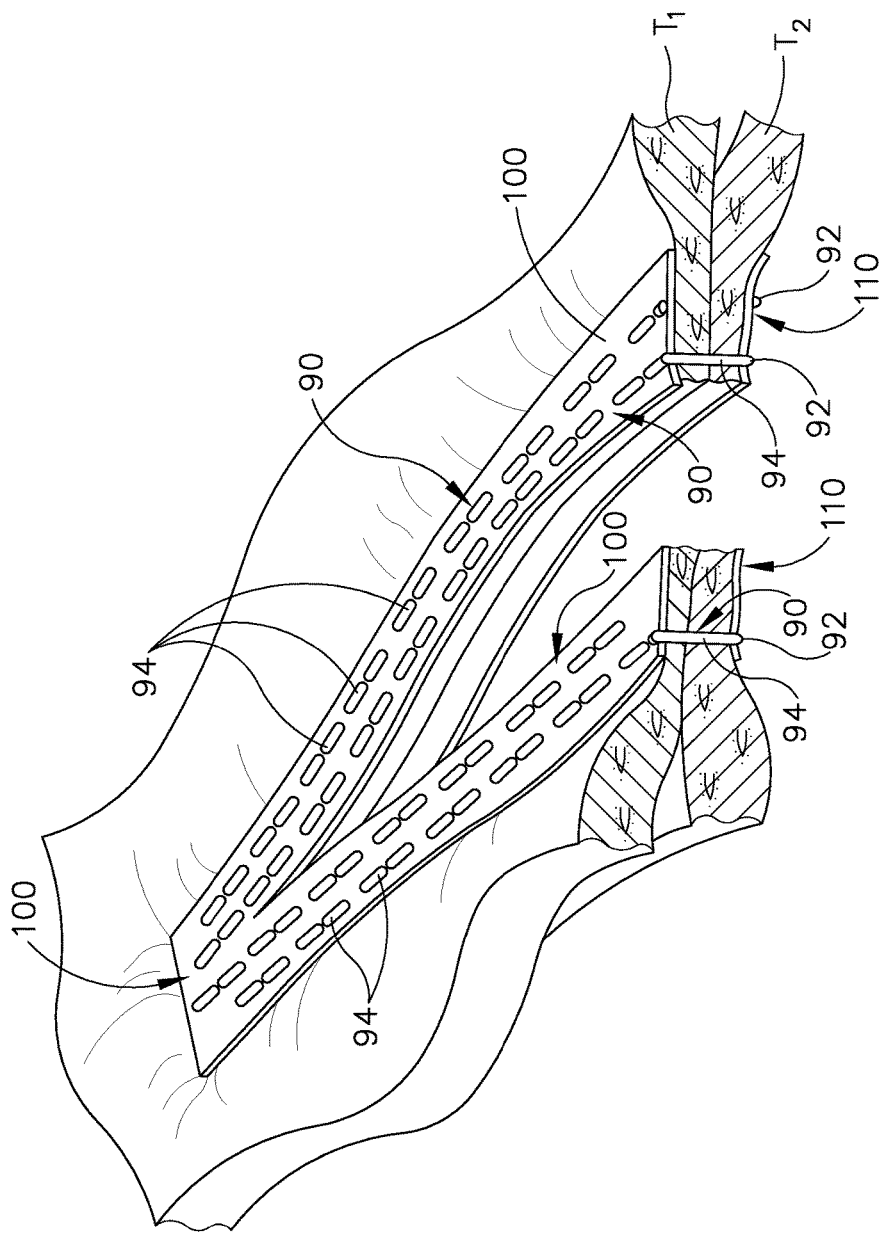
FIG. 6 depicts a perspective view of staples and the buttress assembly of FIG. 5A having been secured to the tissue by the end effector of FIG. 2.

It should be understood that a series of staples (90) will similarly capture and retain buttress assemblies (100, 110) against layers of tissue ($T_1$, $T_2$), thereby securing buttress assemblies (100, 110) to tissue ($T_1$, $T_2$) as shown in FIG. 6. As end effector (40) is pulled away from tissue (90) after deploying staples (90) and buttress assemblies (100, 110), buttress assemblies (100, 110) disengage end effector), such that buttress assemblies (100, 110) remain secured to tissue ($T_1$, $T_2$) with staples (90). Buttress tissue ($T_1$, $T_2$) thus provide structural reinforcement to the lines of staples (90).

As can also be seen in FIG. 6, knife member (80) also cuts through a centerline of buttress tissue assemblies (100, 110), separating each buttress assemblies (100, 110) into a corresponding pair of sections, such that each section remains secured to a respective severed region of tissue ($T_1$, $T_2$).

Figure 7:
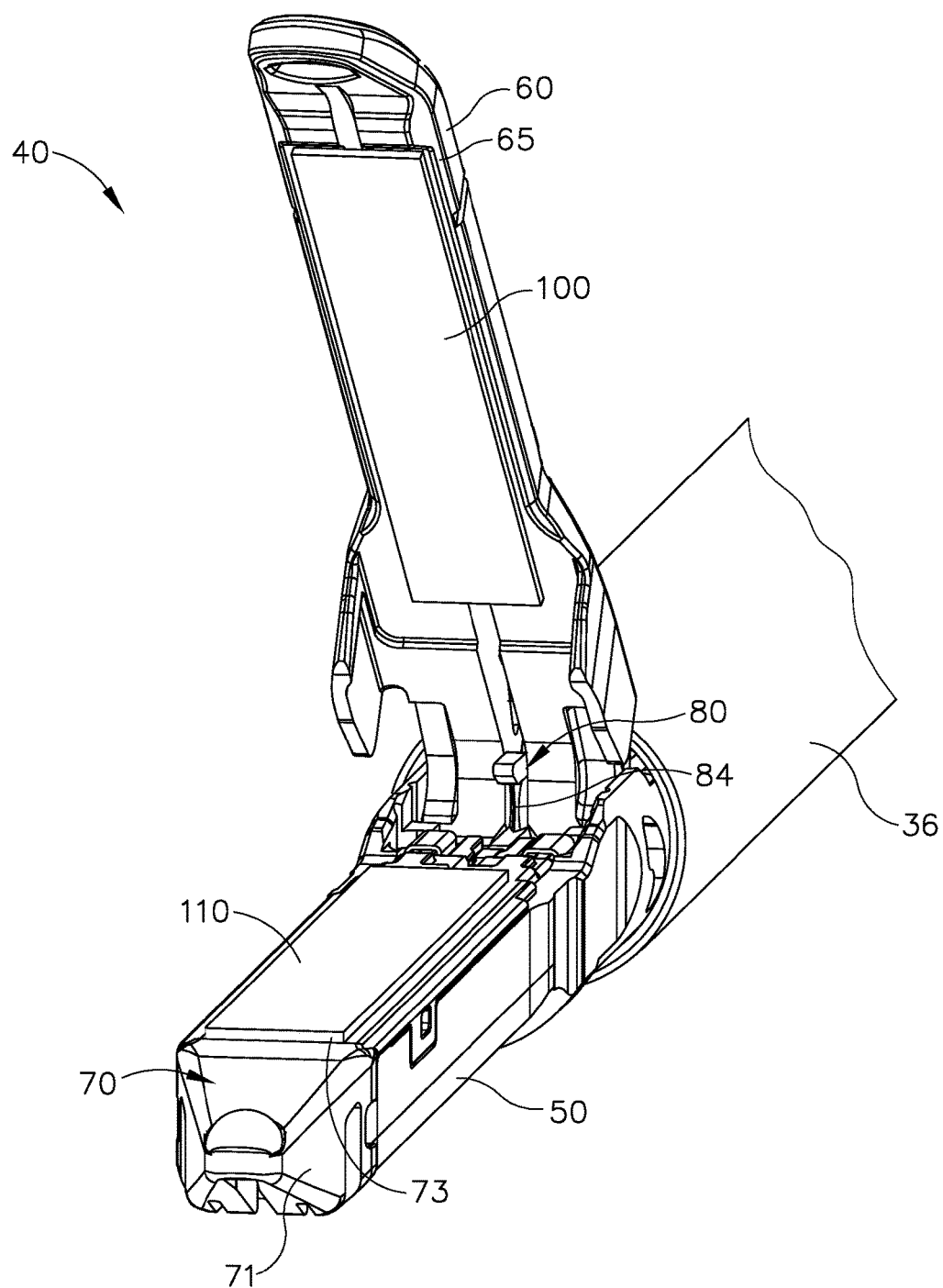
FIG. 7 depicts a perspective view of the upper buttress and the lower buttress of FIG. 4 applied to the end effector of FIG. 2.
Figure 8:
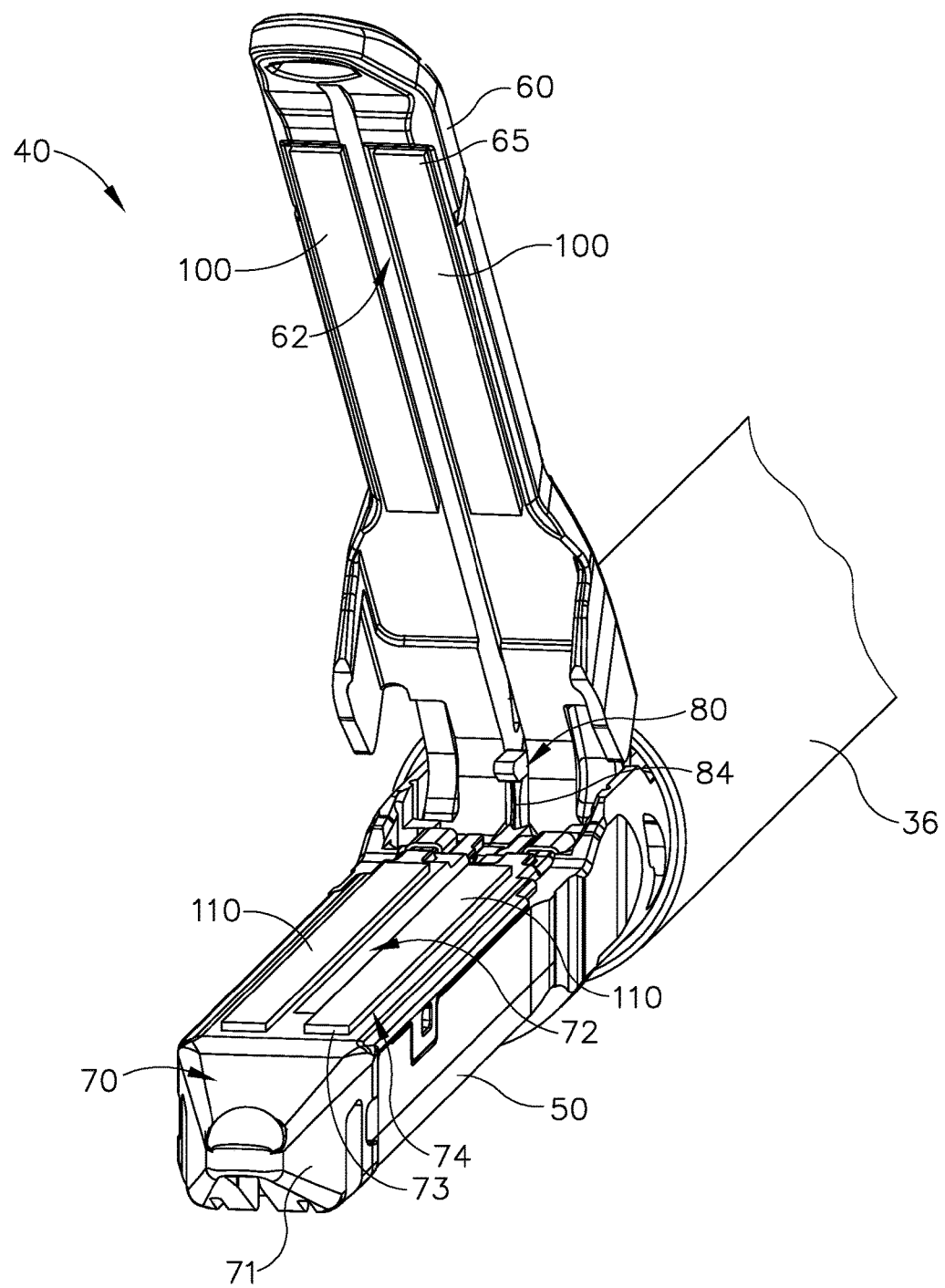
FIG. 8 depicts a perspective view of the upper buttress and the lower buttress of FIG. 4 applied to the end effector of FIG. 2 with a gap on the upper buttress and the lower buttress for the longitudinally extending channels of the end effector.

In the foregoing example, as shown in FIG. 7, buttress assembly (100) is sized to span across the full width of underside (65), such that buttress assembly (100) spans across channel (62). Thus, knife member (80) cuts through buttress assembly (100) during actuation of end effector (40) as described above. In some other examples, as shown in FIG. 8, such as those described below, buttress assembly (100) is provided in two separate, laterally spaced apart portions, with one portion being disposed on underside (65) on one side of channel (62) and another portion being disposed on underside (65) on the other side of channel (62). In such versions, buttress assembly (100) does not span across channel (62), such that knife member (80) does not cut through buttress assembly (100) during actuation of end effector (40).

Likewise, as also shown in FIG. 7, buttress assembly (110) may be sized to span across the full width of deck (73), such that buttress assembly (110) spans across channel (72), and such that knife member (80) cuts through buttress assembly (110) during actuation of end effector (40) as described above. Alternatively, as also shown in FIG. 8, buttress assembly (110) may be provided in two separate, laterally spaced apart portions, with one portion being disposed on deck (73) on one side of channel (72) and another portion being disposed on deck (73) on the other side of channel (72), such that buttress assembly (110) does not span across channel (72), and such that knife member (80) does not cut through buttress assembly (110) during actuation of end effector (40).

III. Exemplary Multilayer Buttress Body

In some instances, it may be desirable to have a multilayer buttress body instead of one uniform buttress body (102, 112) attached to adhesive layer (104, 114). A buttress body with multiple layers may provide added benefits stemming from the diverse material properties of each layer, either while attached to end effector (70) via adhesive layer (104, 1140) or while attached to tissue ($T_1$, $T_2$) via staples (90). For example, one layer may be utilized to provide the benefit of tissue reinforcement while another layer may be utilized to further promote hemostasis or a combination thereof. Additionally or alternatively, placement of multiple layers relative to each other may provide additional benefits. For instance, a first layer may be placed between adhesive layer (104, 114) and a second layer in order to allow adhesive layer (104, 114) to better adhere to underside (65) of anvil (60) and/or deck (73) of staple cartridge (70). Various examples of multilayer buttress bodies will be described in greater detail below. It should be understood that the following examples may be used in place of buttress assemblies (100, 110) described above.

A. Multilayer Buttress Body with Continuous Film Layer

FIG. 10 shows a multilayer buttress assembly (200) including a multilayer buttress body (202) and an adhesive layer (204). Multilayer buttress assembly (200) may be used with end effector (40) in place of either or both buttress assemblies (100, 110) as mentioned above. Therefore, adhesive layer (204) may be substantially similar to adhesive layers (104, 114) mentioned above. As such, multilayer buttress assembly (200) may be adhered to underside (65) of anvil (60) and/or deck (73) of staple cartridge (70). The material forming adhesive layer (204) may provide proper positioning of multilayer buttress body (202) before and during actuation of end effector (40); then allow multilayer buttress body (202) to separate from end effector (40) after end effector (40) has been actuated, without causing damage to multilayer buttress body (202) that is substantial enough to compromise the proper subsequent functioning of multilayer buttress body (202). By way of example only, adhesive layer (204) may be constructed and operable in accordance with at least some of the teachings of U.S. patent application Ser. No. 14/667,842, entitled "Method of Applying a Buttress to a Surgical Stapler," filed Mar. 25, 2015, published as U.S. Pat. No. 2016/0278774 on Sep. 26, 2016, the disclosure of which is incorporated by reference herein.

FIGS. 9-10 show multilayer buttress body (202) including a mesh layer (206) and a film layer (208). Film layer (208) may comprise any suitable bioabsorbable materials, including but not limited to PDS (polydioxanone), polyglactin 910, or polyglecaprone 25. Various other suitable materials that may be used will be apparent to those of ordinary skill in the art in view of the teachings herein. Film layer (208) is integrally connected to mesh layer (206) and lies on top of mesh layer (206). Film layer (208) may be integrally connected to mesh layer (206) through a heated press, combining pressure and heat. It should be understood film layer (208) is a continuous film with minimal porosity in the present example. In other words, film layer (208) prevents fluid from traveling across its boundaries.

As shown in FIG. 9, mesh layer (206) is a two dimensional planar construct allowing minimal stretching. Mesh layer (206) may be made of planar fabrics (207) that are combined in a matrix. The matrix formed of planar fabrics (207) may be knitted or woven together in a pattern, or in a random association. FIG. 9 shows matrix formed of planar fabrics (207) knitted or woven in a square texture pattern. However, any number of suitable texture patterns may be used as would be apparent to a person having ordinary skill in the art in view of the teachings herein.

While FIG. 9 shows mesh layer (206) in a two dimensional planar construct, it is envisioned mesh layer (206) may form a three dimensional mesh layer construct in some other versions. For instance, a three dimensional version of mesh layer (206) may be made out of knitted spacer fabrics, Rachel knitted spacer fabrics, uncut velvet, terry cloth, or any other suitable material as will be apparent to a person having ordinary skill in the art in view of the teachings herein. A three dimensional version of mesh layer (206) may allow for minimal extensibility in one direction and spring-like extensibility in a perpendicular direction. The direction with minimal extensibility could be utilized for reinforcement of recently severed tissue ($T_1$, $T_2$); while the spring-like extensibility could be utilized in order to compensate for tissue deformation after end effector (40) severs and staples tissue as described above.

As shown in FIG. 10, film layer (208) is adhered under adhesive layer (204). Due to film layer (208) being interposed between mesh layer (206) and adhesive layer (204) in combination with the continuous nature and minimal porosity of film layer (208), film layer (208) may act as a sealed barrier between mesh layer (206) and adhesive layer (204). In other words, fluids are prevented from passing through film layer (208) in this example. Therefore, if adhesive layer (204) became viscous, film layer (208) may prevent adhesive layer (204) from penetrating into mesh layer (206). This may prevent the viscous nature or adhesive layer (204) from spreading too thin, which may compromise the adhesion between multilayer buttress assembly (200) and end effector (40). In addition, moisture (e.g., bodily fluid, saline, etc.) obtained through mesh layer (206) may not penetrate onto adhesive layer (204). This may allow adhesive layer (204) to properly adhere to underside (65) of anvil (60) or deck (73) of staple cartridge (70) for longer periods of time in a moist environment, such as a surgical site.

It should be understood that because film layer (208) acts as a barrier between mesh layer (206) and adhesive layer (204), mesh layer (206) will be the portion of multilayer buttress body (202) in contact with tissue ($T_1$, $T_2$) when end effector (40) clamps, severs, and staples tissue ($T_1$, $T_2$) as described above when utilizing multilayer buttress assembly (200). Therefore, film layer (208) will be closer to underside (65) of anvil (60) and/or deck (73) of staple cartridge (70). If multilayer buttress assembly (200) is used on both underside (65) of anvil (60) and deck (73) of staple cartridge (70), a pair of film layers (208) would be surrounding both tissue ($T_1$, $T_2$) and mesh layers (206). This geometry surrounding tissue ($T_1$, $T_2$) may help prevent tissue ($T_1$, $T_2$) from forming an adhesion at the site of stapling and severing.

Film layer (208) may be made out of a material that is conformable. In other words, once film layer (208) is punctured by staples (90), film layer (208) conforms around staple (90) and forms a seal around the portion of staple legs (94) penetrating film layer (208). This may allow for film layer (208) to still act as a barrier after multilayer buttress (200) is detached from end effector (40) and attached to tissue ($T_1$, $T_2$) via staples (90) as shown in FIG. 6. This sealing effect may enhance hemostasis. Also, due to the continuous nature and minimal porosity of film layer (208), film layer (208) may also spread pressure from driven staples (90) on a more uniform area of compression on tissue ($T_1$, $T_2$), also potentially enhancing hemostasis.

If multilayer buttress assembly (200) is located on deck (73) of staple cartridge (70), film layer (208) may also act as a barrier between tissue ($T_1$, $T_2$) and deck (73) of staple cartridge (70). As described above, deck (73) houses staples (90), which are driven by staple driver (75). Tissue ($T_1$, $T_2$) may exert fluids or flowing tissue into deck (73) when compressed by anvil (60) pivoting towards lower jaw (50). These fluids or flowing tissue may impart of force on individual staples (90) located within deck (73), creating a misalignment between staple crown (92) and staple driver (75). This misalignment may lead to a higher probability of staple legs (94) hitting staple forming pockets (64) in an unintended orientation, possibly leading to an inadequate staple formation. However, the sealed barrier created by film layer (208) may prevent tissue ($T_1$, $T_2$) exerting fluid or flowing tissue into deck (73), thereby increasing the probability of a proper staple (90) forming against staple forming pocket (64).

Additionally, when end effector (40) clamps, severs, and staples tissue ($T_1$, $T_2$), staples (90) will travel through planar fabrics (207) of mesh layer (206), potentially confining staple legs (94) within the matrix defined by mesh layer (206). This confinement may allow mesh layer (206) to help interlock individual staples (90) in such a way that staples (90) act as a group. The confinement of staples (90) may also allow mesh layer (206) to absorb and distribute loads provided by driving staples (90) that would otherwise be directly transferred to tissue ($T_1$, $T_2$), which may help prevent tissue failure due to overstress.

In some exemplary variations of buttress assembly (200), another film layer may be positioned under mesh layer (206). By way of example only, this additional film layer may be configured and operable just like film layer (208) described above. Mesh layer (206) may thus be interposed between two film layers (208). By way of further example only, the additional film layer may be added for increased reinforcement strength, increased stiffness, reduced overall porosity, reduced friction or increased adhesion to adhesive layer.

B. Multilayer Buttress Body with Punctured Film Layer

FIG. 11 shows a multilayer buttress assembly (300) including a multilayer buttress body (302) and an adhesive layer (304). Multilayer buttress assembly (300) may be used with end effector (40) in place of either or all buttress assemblies (100, 110, 200) mentioned above. Therefore, adhesive layer (304) may be substantially similar to adhesive layers (104, 114, 204) mentioned above. As such, multilayer buttress assembly (300) may be adhered to underside (65) of anvil (60) and/or deck (73) of staple cartridge (70). The material forming adhesive layer (304) may provide proper positioning of multilayer buttress body (302) before and during actuation of end effector (40); then allow multilayer buttress body (302) to separate from end effector (40) after end effector (40) has been actuated, without causing damage to multilayer buttress body (302) that is substantial enough to compromise the proper subsequent functioning of multilayer buttress body (302). By way of example only, adhesive layer (304) may be constructed and operable in accordance with at least some of the teachings of U.S. patent applicatio Ser. No. 14/667,842, entitled "Method of Applying a Buttress to a Surgical Stapler," filed Mar. 25, 2015, published as U.S. Pub. No. 2016/0278774 on Sep. 29, 2016, the disclosure of which is incorporated by reference herein.

FIGS. 11-12 show multilayer buttress body (302) including a mesh layer (306) and a film layer (308) interposed between mesh layer (306) and adhesive layer (304). Mesh layer (306) further includes a bottom mesh portion (324), a top mesh portion (322), and a plurality of open loops (326) extending from top mesh portion (322). As will be described in further detail below, loops (326) may extend within and/or through film layer (308) in order to promote attachment between adhesive layer (304) and mesh layer (306). Therefore, unlike multilayer buttress assembly (200) described above, mesh layer (306) could be designed to have some fluid communication with adhesive layer (304). Loops (326) may be formed on top mesh portion (322) through various methods, such as needle tufting, sewing through top mesh portion (322) with a thread, or any other suitable methods as will be apparent to a person having ordinary skill in the art in view of the teachings herein. It should be understood that loops (326) are merely optional in order to promote attachment between adhesive layer (304) and mesh layer (306). For instance, instead of loops (326), top mesh portion (322) may have strings extending from top mesh portion (322) to promote attachment between adhesive layer (304) and mesh layer (306).

Mesh layer (306) forms a three dimensional mesh layer construct. Three dimensional mesh layer (306) may be made out of knitted spacer fabrics, Rachel knitted spacer fabrics, uncut velvet, terry cloth, or any other suitable material as will be apparent to a person having ordinary skill in the art in view of the teachings herein. Fibers forming mesh layer (306) may have surface properties of a multifilament, a monofilament, or any extrudable shapes, any of which could be surface activated for adhesion.

Figure 13B:
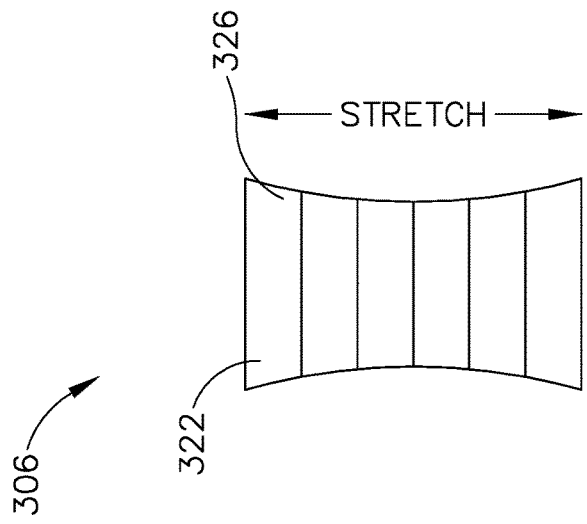
FIG. 13B depicts a top plan view of the mesh layer of the multilayer buttress of FIG. 11 in a stretched position.
Figure 13A:
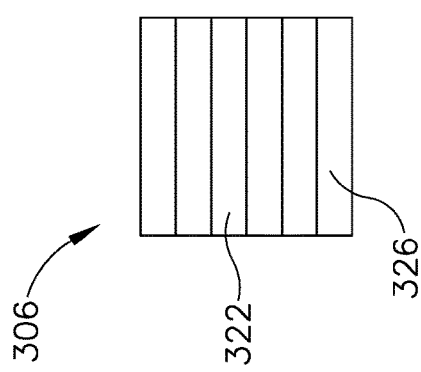
FIG. 13A depicts a top plan view of the mesh layer of the multilayer buttress of FIG. 11 in a relaxed position.

As can be seen in FIGS. 13A-13B, three dimensional mesh layer (306) of the present example has partial elasticity that provides minimal extensibility in one direction (along the plane defined by mesh layer (306)) and spring-like extensibility in a perpendicular direction (also along the plane defined by mesh layer (306)). The direction with minimal extensibility could be utilized for reinforcement of recently severed tissue ($T_1$, $T_2$) while the spring-like extensibility could be utilized in order to compensate for tissue deformation after end effector (40) severs and staples tissue as described above. In the present example, mesh layer (306) is provided in a rectangular shape, with the longer length extending in a longitudinal direction along a corresponding length of end effector (40); and with the shorter width extending in a lateral direction along a corresponding with of end effector (40). Also in the present example, mesh layer (306) has the resilient extensibility in the longitudinal direction and the minimal extensibility in the lateral direction. It should therefore be understood that, after buttress assembly (300) is secured to tissue by staples (90), buttress assembly (300) will be extensible along a path that is parallel to the longitudinal orientation of crowns (92); while being substantially non-extensible along a path that is perpendicular to the longitudinal orientation of crowns (92).

As previously noted, mesh layer (306) includes bottom mesh portion (324) and top mesh portion (322). Bottom mesh portion (324) and top mesh portion (322) may be made out of the same or different material as would be apparent to a person having ordinary skill in the art in view of the teachings herein. However, in the present example, top mesh portion (322) has a greater density as compared to bottom mesh portion (324). The high density of top mesh portion (322) provides reduced porosity of mesh layer (306). Different densities result in different rates of moisture absorption of bottom mesh portion (324) and top mesh portion (322). In particular, the greater density of top mesh portion (322) restricts the amount of moisture absorbed as compared to bottom mesh portion (324). The difference in densities between top mesh portion (322) and bottom mesh portion (324) could be provided through a meltblown process, electrospinning, or any other methods as will be apparent to a person having ordinary skill in the art in view of the teachings herein.

Since top mesh portion (322) is closer to adhesive layer (304), this may result in top mesh portion (322) acting as a semi-permeable barrier. In other words, fluids are somewhat restricted from passing through top mesh portion (322). Therefore, if adhesive layer (304) became viscous, top mesh portion (322) may absorb some of viscous adhesive layer (304) but help prevent adhesive layer (304) from penetrating into bottom mesh portion (324). In addition, top mesh portion (322) may absorb some of the moisture obtained through bottom mesh portion (324) and prevent that moisture from reaching film layer (308). In some versions, top mesh portion (322) may provide some degree of porosity so as to allow water moisture to pass but not allow a viscous adhesive to pass.

It should be understood that because film layer (308) is in contact with adhesive layer (304) and top mesh portion (322) is in contact with film layer (308), bottom mesh portion (324) will be the portion of multilayer buttress body (202) in contact with tissue ($T_1$, $T_2$) when end effector (40) clamps, severs, and staples tissue ($T_1$, $T_2$) as described above when utilizing multilayer buttress assembly (300). Therefore, film layer (208) will be closer to underside (65) of anvil (60) and/or deck (73) of staple cartridge (70). If multilayer buttress assembly (300) is used on both underside (65) of anvil (60) and deck (73) of staple cartridge (70), a pair of film layers (308) would be surrounding both tissue ($T_1$, $T_2$) and mesh layers (206). This geometry surrounding tissue ($T_1$, $T_2$) may help prevent tissue ($T_1$, $T_2$) from forming an adhesion at the site of stapling and severing.

In some examples, film layer (308) may be omitted. In such versions, top mesh portion (322) would be directly interposed between adhesive layer (304) and bottom mesh portion (324). Top mesh portion (322) could be so dense as to absorb some moisture from either bottom mesh portion (324) or adhesive layer (304), but not allow the moisture to saturate top mesh portion (322). This may allow adhesive layer (304) to properly adhere to underside (65) of anvil (60) or deck (73) of staple cartridge (70) for longer periods of time in a moist environment, such as a surgical site.

In some examples, top mesh portion (322) may be so dense that bottom mesh portion (324) would not be needed. In some such versions, top mesh portion (322) would be such a tightly woven mesh that moisture from a viscous adhesive would be able to penetrate mesh layer (306), but not saturate mesh layer (206).

Additionally, when end effector (40) clamps, severs, and staples tissue ($T_1$, $T_2$), staples (90) will travel through mesh layer (306), potentially confining staple legs (94) within the matrix defined by mesh layer (306). This confinement may allow mesh layer (208) to help interlock individual staples (90) in such a way that staples (90) act as a group. The confinement of staples (90) may also allow mesh layer (306) to absorb and distribute loads provided by driving staples (90) that would otherwise be directly transferred to tissue ($T_1$, $T_2$), which may help prevent tissue failure due to overstress.

Film layer (308) is substantially the same as film layer (208), except with possible differences described below. Film layer (308) may comprise any suitable bioabsorbable materials, including but not limited to PDS (polydioxanone), polyglactin 910, or polyglecaprone 25. Various other suitable materials that may be used will be apparent to those of ordinary skill in the art in view of the teachings herein. Film layer (308) is integrally connected to mesh layer (306) and lies on top of mesh layer (306). Film layer (308) may be integrally connected to mesh layer (306) through a heated press, combining pressure and heat. As mentioned above, film layer (308) may allow loops (326) of mesh portion (306) to extend through film layer (308) in order for mesh portion (306) to connect with adhesive layer (304). It should be understood that film layer (308) or any of its alternatives may be utilized in any of the examples described herein. It should also be understood that the porosity of film layer (308) and/or top mesh portion (322) could be sized so water moisture may pass but a viscous adhesive could not.

As shown in FIGS. 14A-14B, unlike film layer (208), a plurality of slits (312) are formed in film layer (308) in the present example. Slits (312) accommodate longitudinal stretching of film layer (308) with mesh layer (306) from a rested position, as shown in FIG. 14A, to a stretched position, as shown in FIG. 14B. Therefore, film layer (308) may stretch longitudinally with mesh portion (306), as shown in FIGS. 13A-13B. Slits (312) allow mesh portion (306) to extend through film layer (308). Additionally, slits (312) permit fluid communication between adhesive portion (304) and mesh portion (306).

As can be seen in FIGS. 15-17, slits (312) are just one of option to provide for selective communication between adhesive portion (304) and mesh portion (306). In particular, FIGS. 15-17 show alternative films (314, 316, 318) that are substantially similar to film layer (308) described above. Alternative films (314, 316, 318) have diamond holes (315), circular holes (317), and a "Z" cut holes (319) respectively, enabling communication between adhesive portion (304) and mesh portion (306). However, the present examples should not be seen as limiting. Slits (312) or holes (315, 317, 319) may have any other suitable shape as will be apparent to a person having ordinary skill in the art in view of the teachings herein.

Figure 20:
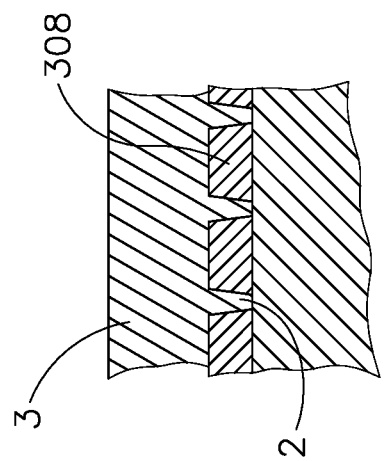
FIG. 20 depicts a partial cross-sectional view of an exemplary method of using a press to form holes in the film layer of the multilayer buttress of FIG. 11.
Figure 19:
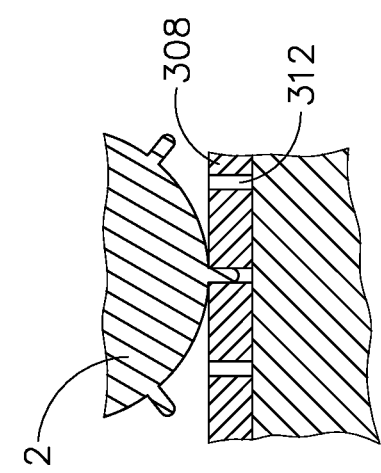
FIG. 19 depicts a partial cross-sectional view of an exemplary method of using a roller to form holes in the film layer of the multilayer buttress of FIG. 11.
Figure 18:
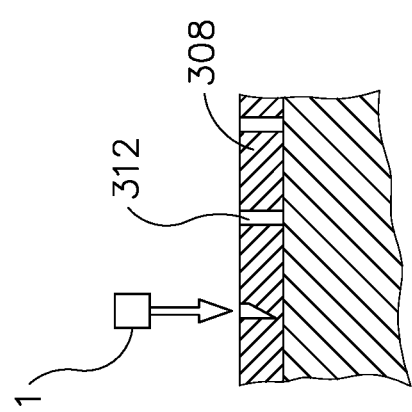
FIG. 18 depicts a partial cross-sectional view of an exemplary method of using a laser to form holes in the film layer of the multilayer buttress of FIG. 11.

It should be understood that various techniques may be used to form slits (312) or holes (315, 317, 319) in film layer (308). For instance, as shown in FIG. 18, a laser (1) may be used to form slits (312) or holes (315, 317, 319) in film layer (308). As another merely illustrative example, a studded roller (2) may be used to form slits (312) or holes (315, 317, 319) in film layer (308), as shown in FIG. 19. Here, roller (2) would roll over film layer (308) to penetrate film layer (308) to form slits (312) or holes (315, 317, 319). Roller (2) would have a diameter and specified frequency of studs about the circumference to determine where slits (312) or holes (315, 317, 319) would be located on film layer (308). As yet another merely illustrative example, a studded press (3) may be used to form slits (312) or holes (315, 317, 319) in film layer (308), as shown in FIG. 20. Here, press (3) would make a plurality of slits (312) or holes (315, 317, 319) with one penetrating move. Of course, any other suitable devices or techniques may be used to create slits (312) or holes (315, 317, 319) as will be apparent to a person having ordinary skill in the art in view of the teachings herein.

In addition to the foregoing, it should also be understood that any of the various buttress assemblies described herein may be further constructed and operable in accordance with at least some of the teachings of U.S. patent application Ser. No. 14/667,842, entitled "Method of Applying a Buttress to a Surgical Stapler," filed Mar. 25, 2015, Published as U.S. Pub. No. 2016/0278774 on Sep. 26, 2016, the disclosure of which is incorporated by reference herein.

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

EXAMPLE 1

An apparatus, comprising: (a) an end effector, wherein the end effector comprises: (i) an anvil, and (ii) a lower jaw, wherein the anvil is configured to move toward and away from the lower jaw; (b) a cartridge, wherein the lower jaw is configured to receive the cartridge, the cartridge comprising: (i) a housing, (ii) a plurality of staples disposed in the housing, and (iii) a deck disposed over the plurality of staples, the deck defining a plurality of apertures, each aperture being substantially disposed over each staple, wherein the end effector is operable to drive the staples through the apertures of the deck toward the anvil; and (c) a buttress assembly configured to be attached to either the anvil or the cartridge, wherein the buttress assembly comprises: (i) an adhesive layer configured to adhere to either the anvil or the deck of the cartridge, (ii) a film layer having a first side and a second side, wherein the first side is attached to the adhesive layer, and (iii) a buttress body attached to the second side of the film layer such that the film layer is interposed between the adhesive layer and the buttress body.

EXAMPLE 2

The apparatus of Example 1, wherein the film layer is configured to prevent moisture from traveling from either the first side to the second side or the second side to the first side.

EXAMPLE 3

The apparatus of Example 2, wherein the plurality of staples are configured to puncture the film layer, wherein the film layer is configured to form a seal around a portion of the plurality of staples puncturing the film layer.

EXAMPLE 4

The apparatus of any one or more of Examples 1 through 3, wherein the buttress body comprises a plurality of planar fabrics.

EXAMPLE 5

The apparatus of Example 4, wherein the plurality of planar fabrics are woven or knitted.

EXAMPLE 6

The apparatus of any one or more of Examples 1 through 3=5, wherein the buttress body comprises a three dimensional mesh.

EXAMPLE 7

The apparatus of Example 6, wherein the three dimensional mesh and the film layer are both configured to stretch along an axis.

EXAMPLE 8

The apparatus of any one or more of Examples 6 through 7, wherein the three dimensional mesh comprises a top portion and a bottom portion, wherein the top portion comprises a third face, wherein the third face is fixed to the second side of the film layer.

EXAMPLE 9

The apparatus of Example 8, wherein the bottom portion comprises a fourth face, wherein the fourth face is configured to contact tissue captured between the anvil and the deck of the staple cartridge.

EXAMPLE 10

The apparatus of Example 9, wherein the top portion and the bottom portion have different densities.

Example 11

The apparatus of any one or more of Examples 6 through 10, wherein the film comprises a plurality of holes extending from the first side to the second side.

EXAMPLE 12

The apparatus of Example 11, wherein the buttress body comprises a third side fixed to the second side of film layer, wherein the buttress body further comprises a plurality of fibers extending from the third side into the plurality of holes.

EXAMPLE 13

The apparatus of Example 12, wherein the plurality of fibers are fixed to the adhesive layer.

EXAMPLE 14

The apparatus of Example 13, wherein the plurality of fibers form loops within the buttress body.

EXAMPLE 15

The apparatus of any one or more of Examples 1 through 14, wherein the anvil of the end effector defines a first longitudinally extending channel, wherein the cartridge defines a second longitudinally extending channel corresponding to the first longitudinally extending channel.

EXAMPLE 16

The apparatus of Example 15, wherein the buttress assembly extends across either the first longitudinally extending channel or the second longitudinally extending channel.

EXAMPLE 17

The apparatus of Example 16, wherein the buttress does not extend across either the first longitudinally extending channel or the second longitudinally extending channel.

EXAMPLE 18

An apparatus, comprising: (a) an end effector, wherein the end effector comprises: (i) an anvil, and (ii) a lower jaw, wherein the anvil is configured to move toward and away from the lower jaw; (b) a cartridge, wherein the lower jaw is configured to receive the cartridge, the cartridge comprising: (i) a housing, (ii) a plurality of staples disposed in the housing, and (iii) a deck disposed over the plurality of staples, the deck defining a plurality of apertures, each aperture being substantially disposed over each staple, wherein the end effector is operable to drive the staples through the apertures of the deck toward the anvil; and (c) a buttress assembly configured to be attached to either the anvil or the cartridge, wherein the buttress assembly comprises: (i) an adhesive layer configured to adhere to either the anvil or the deck of the cartridge, and (ii) a buttress body, wherein the adhesive layer is laid over the buttress body, wherein the buttress body comprises: (A) a top mesh portion, and (B) a bottom mesh portion, wherein the top mesh portion has a first density and the bottom mesh portion has a second density, wherein the first density and the second density are different.

EXAMPLE 19

The apparatus of Example 18, wherein the top mesh portion comprises a first face and a second face, wherein the first face of the top mesh portion is attached to the adhesive layer, wherein the second face of the top mesh portion is fixed to the bottom mesh portion.

EXAMPLE 20

An apparatus, comprising: (a) an end effector, wherein the end effector comprises: (i) an anvil, and (ii) a lower jaw, wherein the anvil is configured to move toward and away from the lower jaw; (b) a cartridge, wherein the lower jaw is configured to receive the cartridge, the cartridge comprising: (i) a housing, (ii) a plurality of staples disposed in the housing, and (iii) a deck disposed over the plurality of staples, the deck defining a plurality of apertures, each aperture being substantially disposed over each staple, wherein the end effector is operable to drive the staples through the apertures of the deck toward the anvil; and (c) a buttress assembly configured to be attached to either the anvil or the cartridge, wherein the buttress assembly comprises: (i) an adhesive layer configured to adhere to either the anvil or the deck of the cartridge, wherein the adhesive layer is configured to become viscous when attaching to either the anvil or the cartridge, and (ii) a buttress body attached to the adhesive layer, wherein the buttress body comprises a mesh having a density sufficient to allow the viscous adhesive layer to penetrate the buttress body but not saturate the buttress body.

V. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

In addition to the foregoing, it should also be understood that any of the various buttress assemblies described herein may be further constructed and operable in accordance with at least some of the teachings of U.S. patent application Ser. No. 14/667,842, entitled "Method of Applying a Buttress to a Surgical Stapler," filed Mar. 25, 2015, published as U.S. Pub. No. 2016/0278774 on Sep. 26, 2016, the disclosure of which is incorporated by reference herein; U.S. patent application Ser. No. 14/827,856, entitled "Implantable Layers for a Surgical Instrument," filed Aug. 17, 2015, published as U.S. Pub. No. 2017/0049444 on Feb. 23, 2017, the disclosure of which is incorporated by reference herein; U.S. patent application Ser. No. 14/871,071, entitled "Compressible Adjunct with Crossing Spacer Fibers," filed Sep. 30, 2015, published as U.S. Pub. No. 2017/0086837 on Mar. 30, 2017, the disclosure of which is incorporated by reference herein; and U.S. patent application Ser. No. 14/871,131, entitled "Method for Applying an Implantable Layer to a Fastener Cartridge," filed Sep. 30, 2015, published as U.S. Pub. No. 2017/0086842 on Mar. 30, 2017, the disclosure of which is incorporated by reference herein. Furthermore, in addition to the methods described herein, any of the various buttress assemblies described herein may be applied to end effector (40) in accordance with at least some of the teachings of U.S. Provisional Patent App. No. 62/209,041, entitled "Method and Apparatus for Applying a Buttress to End Effector of a Surgical Stapler," filed Aug. 24, 2015, the disclosure of which is incorporated by reference herein;

and/or U.S. patent application Ser. No. 14/871,131, entitled "Method for Applying an Implantable Layer to a Fastener Cartridge," filed Sep. 30, 2015, published as U.S. Pub. No. 2017/0086842 on Mar. 30, 2017, the disclosure of which is incorporated by reference herein. Various suitable ways in which the teachings herein may be combined with various teachings of the above-cited references will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; U.S. Pub. No. 2013/0012957, entitled "Automated End Effector Component Reloading System for Use with a Robotic System, published Jan. 10, 2013, issued as U.S. Pat. No. 8,844,7879 on Sep. 30, 2014, the disclosure of which is incorporated by reference herein; U.S. Pub. No. 2012/0199630, entitled "Robotically-Controlled Surgical Instrument with Force-Feedback Capabilities," published Aug. 9, 2012, issued as U.S. Pat. No. 8,820,605 on Sep. 2, 2014, the disclosure of which is incorporated by reference herein; U.S. Pub. No. 2012/0132450, entitled "Shiftable Drive Interface for Robotically-Controlled Surgical Tool," published May 31, 2012, issued as U.S. Pat. No. 8,616,431 on Dec. 31, 2013, the disclosure of which is incorporated by reference herein; U.S. Pub. No. 2012/0199633, entitled "Surgical Stapling Instruments with Cam-Driven Staple Deployment Arrangements," published Aug. 9, 2012, issued as U.S. Pat. No. 8,573,461 on Nov. 5, 2013, the disclosure of which is incorporated by reference herein; U.S. Pub. No. 2012/0199631, entitled "Robotically-Controlled Motorized Surgical End Effector System with Rotary Actuated Closure Systems Having Variable Actuation Speeds," published Aug. 9, 2012, issued as U.S. Pat. No. 8,602,288 on Dec. 10, 2013, the disclosure of which is incorporated by reference herein; U.S. Pub. No. 2012/0199632, entitled "Robotically-Controlled Surgical Instrument with Selectively Articulatable End Effector," published Aug. 9, 2012, issued as U.S. Pat. No. 9,301,759 on Apr. 5, 2016, the disclosure of which is incorporated by reference herein; U.S. Pub. No. 2012/0203247, entitled "Robotically-Controlled Surgical End Effector System," published Aug. 9, 2012, issued as U.S. Pat. No. 8,783,541 on Jul. 22, 2014, the disclosure of which is incorporated by reference herein; U.S. Pub. No. 2012/0211546, entitled "Drive Interface for Operably Coupling a Manipulatable Surgical Tool to a Robot," published Aug. 23, 2012 issued as U.S. Pat. No. 8,479,969 on Jul. 9, 2013; U.S. Pub. No. 2012/0138660, entitled "Robotically-Controlled Cable-Based Surgical End Effectors," published Jun. 7, 2012, issued as U.S. Pat. No. 8,800,838 on Aug. 12, 2014, the disclosure of which is incorporated by reference herein; and/or U.S. Pub. No. 2012/0205421, entitled "Robotically-Controlled Surgical End Effector System with Rotary Actuated Closure Systems," published Aug. 16, 2012, issued as U.S. Pat. No. 8,573,465 on Nov. 5, 2013, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus, comprising:
   (a) an end effector, wherein the end effector comprises:
      (i) an anvil, and
      (ii) a lower jaw, wherein the anvil is configured to move toward and away from the lower jaw;
   (b) a cartridge, wherein the lower jaw is configured to receive the cartridge, the cartridge comprising:
      (i) a housing,
      (ii) a plurality of staples disposed in the housing, and
      (iii) a deck disposed over the plurality of staples, the deck defining a plurality of apertures, each aperture being substantially disposed over each staple, wherein the end effector is operable to drive the staples through the apertures of the deck toward the anvil; and
   (c) a buttress assembly configured to be attached to either the anvil or the cartridge, wherein the buttress assembly comprises:
      (i) an adhesive layer configured to adhere to either the anvil or the deck of the cartridge,
      (ii) a film layer having a first side and a second side, wherein the first side is attached to the adhesive layer, and
      (iii) a buttress body attached to the second side of the film layer such that the film layer is interposed between the adhesive layer and the buttress body;
   wherein the plurality of staples are configured to puncture the film layer, wherein the film layer is configured to form a seal around a portion of the plurality of staples puncturing the film layer to prevent the adhesive or fluid from flowing past the film layer along portions of the staples that puncture the film layer.

2. The apparatus of claim 1, wherein the film layer is configured to prevent moisture from traveling from either the first side to the second side or the second side to the first side.

3. The apparatus of claim 1, wherein the buttress body comprises a plurality of planar fabrics.

4. The apparatus of claim 1, wherein the plurality of planar fabrics are woven or knitted.

5. The apparatus of claim 1, wherein the buttress body comprises a three dimensional mesh.

6. The apparatus of claim 5, wherein the three dimensional mesh and the film layer are both configured to stretch along an axis.

7. The apparatus of claim 5, wherein the three dimensional mesh comprises a top portion and a bottom portion, wherein the top portion comprises a third face, wherein the third face is fixed to the second side of the film layer.

8. The apparatus of claim 7, wherein the bottom portion comprises a fourth face, wherein the fourth face is configured to contact tissue captured between the anvil and the deck of the staple cartridge.

9. The apparatus of claim 8, wherein the top portion and the bottom portion have different densities.

10. The apparatus of claim 5, wherein the film comprises a plurality of holes extending from the first side to the second side.

11. The apparatus of claim 10, wherein the buttress body comprises a third side fixed to the second side of film layer, wherein the buttress body further comprises a plurality of fibers extending from the third side into the plurality of holes.

12. The apparatus of claim 11, wherein the plurality of fibers are fixed to the adhesive layer.

13. The apparatus of claim 12, wherein the plurality of fibers form loops within the buttress body.

14. The apparatus of claim 1, wherein the anvil of the end effector defines a first longitudinally extending channel, wherein the cartridge defines a second longitudinally extending channel corresponding to the first longitudinally extending channel.

15. The apparatus of claim 14, wherein the buttress assembly extends across either the first longitudinally extending channel or the second longitudinally extending channel.

16. The apparatus of claim 15, wherein the buttress does not extend across either the first longitudinally extending channel or the second longitudinally extending channel.

17. An apparatus, comprising:
   (a) an end effector, wherein the end effector comprises:
      (i) an anvil, and
      (ii) a lower jaw, wherein the anvil is configured to move toward and away from the lower jaw;
   (b) a cartridge, wherein the lower jaw is configured to receive the cartridge, the cartridge comprising:
      (i) a housing,
      (ii) a plurality of staples disposed in the housing, and
      (iii) a deck disposed over the plurality of staples, the deck defining a plurality of apertures, each aperture being substantially disposed over each staple, wherein the end effector is operable to drive the staples through the apertures of the deck toward the anvil; and
   (c) a buttress assembly configured to be attached to either the anvil or the cartridge, wherein the buttress assembly comprises:
      (i) an adhesive layer configured to adhere to either the anvil or the deck of the cartridge, and
      (ii) a buttress body, wherein the adhesive layer is laid over the buttress body, wherein the buttress body comprises:
         (A) a top mesh portion, and
         (B) a bottom mesh portion, wherein the top mesh portion has a first density and the bottom mesh portion has a second density, wherein the first density and the second density are different;
   wherein the top mesh portion comprises a first face and a second face, wherein the first face of the top mesh portion is attached to the adhesive layer, wherein the second face of the top mesh portion is fixed to the bottom mesh portion and wherein the difference between the first density and the second density are configured to result in different rates of moisture absorption across the buttress body.

18. An apparatus, comprising:
(a) an end effector, wherein the end effector comprises:
   (i) an anvil, and
   (ii) a lower jaw, wherein the anvil is configured to move toward and away from the lower jaw;
(b) a cartridge, wherein the lower jaw is configured to receive the cartridge, the cartridge comprising:
   (i) a housing,
   (ii) a plurality of staples disposed in the housing, and
   (iii) a deck disposed over the plurality of staples, the deck defining a plurality of apertures, each aperture being substantially disposed over each staple, wherein the end effector is operable to drive the staples through the apertures of the deck toward the anvil; and
(c) a buttress assembly configured to be attached to either the anvil or the cartridge, wherein the buttress assembly comprises:
   (i) an adhesive layer configured to adhere to either the anvil or the deck of the cartridge, wherein the adhesive layer is configured to become viscous when attaching to either the anvil or the cartridge, and
   (ii) a buttress body attached to the adhesive layer, wherein the buttress body comprises a mesh having a density to allow the viscous adhesive layer to penetrate the buttress body but not saturate the buttress body.

* * * * *